US012740767B2

(12) United States Patent
Usuda

(10) Patent No.: US 12,740,767 B2
(45) Date of Patent: Sep. 22, 2026

(54) DIAGNOSTIC ASSISTANCE APPARATUS, ULTRASOUND ENDOSCOPE, DIAGNOSTIC ASSISTANCE METHOD, AND PROGRAM

(71) Applicant: FUJIFILM CORPORATION, Tokyo (JP)

(72) Inventor: Toshihiro Usuda, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 0 days.

(21) Appl. No.: 18/964,697

(22) Filed: Dec. 2, 2024

(65) Prior Publication Data

US 2025/0090145 A1 Mar. 20, 2025

Related U.S. Application Data

(63) Continuation of application No. PCT/JP2023/020699, filed on Jun. 2, 2023.

(30) Foreign Application Priority Data

Jun. 29, 2022 (JP) ................................ 2022-105151

(51) Int. Cl.
*A61B 8/00* (2006.01)
*A61B 8/12* (2006.01)

(52) U.S. Cl.
CPC .............. *A61B 8/5223* (2013.01); *A61B 8/12* (2013.01); *A61B 8/469* (2013.01); *A61B 8/5207* (2013.01); *A61B 8/5246* (2013.01); *A61B 8/54* (2013.01)

(58) Field of Classification Search
CPC ......... A61B 8/5223; A61B 8/12; A61B 8/469; A61B 8/5207; A61B 8/5246; A61B 8/54; A61B 8/463; A61B 8/485; A61B 8/488
See application file for complete search history.

(56) References Cited

U.S. PATENT DOCUMENTS

2015/0087980 A1* 3/2015 Yao ........................ A61B 8/463 600/440
2016/0012572 A1* 1/2016 Min .......................... G06T 5/92 345/589

(Continued)

FOREIGN PATENT DOCUMENTS

JP 2021-007512 A 1/2021
JP 2021-035442 A 3/2021

(Continued)

OTHER PUBLICATIONS

International Search Report issued in International Application No. PCT/JP2023/020699 on Jul. 4, 2023.

(Continued)

*Primary Examiner* — Kaitlyn E Sebastian
(74) *Attorney, Agent, or Firm* — SOLARIS Intellectual Property Group, PLLC

(57) ABSTRACT

A diagnostic assistance apparatus includes a processor. The processor is configured to acquire a first ultrasound image generated by an ultrasound module, and switch between a first operating mode and a second operating mode according to whether or not reference information is combined with the first ultrasound image, according to whether or not the first ultrasound image is an image obtained in an auxiliary image mode, or according to a set value that stipulates the image quality of the first ultrasound image. The first operating mode is an operating mode that performs detection of a specific area on the basis of detection assistance information created using a second ultrasound image obtained in a main image mode. The second operating mode is an operating mode that performs detection of the specific area but does not output a detection result, or that does not perform detection of the specific area.

20 Claims, 19 Drawing Sheets

(56) References Cited

U.S. PATENT DOCUMENTS

| | | | |
|---|---|---|---|
| 2017/0360415 | A1* | 12/2017 | Rothberg ............. A61B 8/4477 |
| 2020/0000439 | A1* | 1/2020 | Satoh ....................... A61B 8/58 |
| 2020/0126223 | A1* | 4/2020 | Kitamura ......... A61B 1/000094 |
| 2020/0146529 | A1 | 5/2020 | Kono et al. |
| 2020/0178846 | A1* | 6/2020 | Matsumoto .......... A61B 8/5223 |
| 2020/0320702 | A1 | 10/2020 | Kamon |
| 2021/0153730 | A1 | 5/2021 | Karino |
| 2021/0161506 | A1 | 6/2021 | Ito |
| 2021/0219944 | A1* | 7/2021 | Akkus .................... A61B 8/485 |
| 2022/0401075 | A1* | 12/2022 | Sato .................... G01S 7/52046 |

FOREIGN PATENT DOCUMENTS

| | | | |
|---|---|---|---|
| JP | 2021-083699 | A | 6/2021 |
| JP | 2021-186257 | A | 12/2021 |
| WO | 2018/198327 | A1 | 11/2018 |
| WO | 2019/016912 | A1 | 1/2019 |
| WO | 2019/138773 | A1 | 7/2019 |
| WO | 2020/036121 | A1 | 2/2020 |

OTHER PUBLICATIONS

Written Opinion of the ISA issued in International Application No. PCT/JP2023/020699 on Jul. 4, 2023.

* cited by examiner

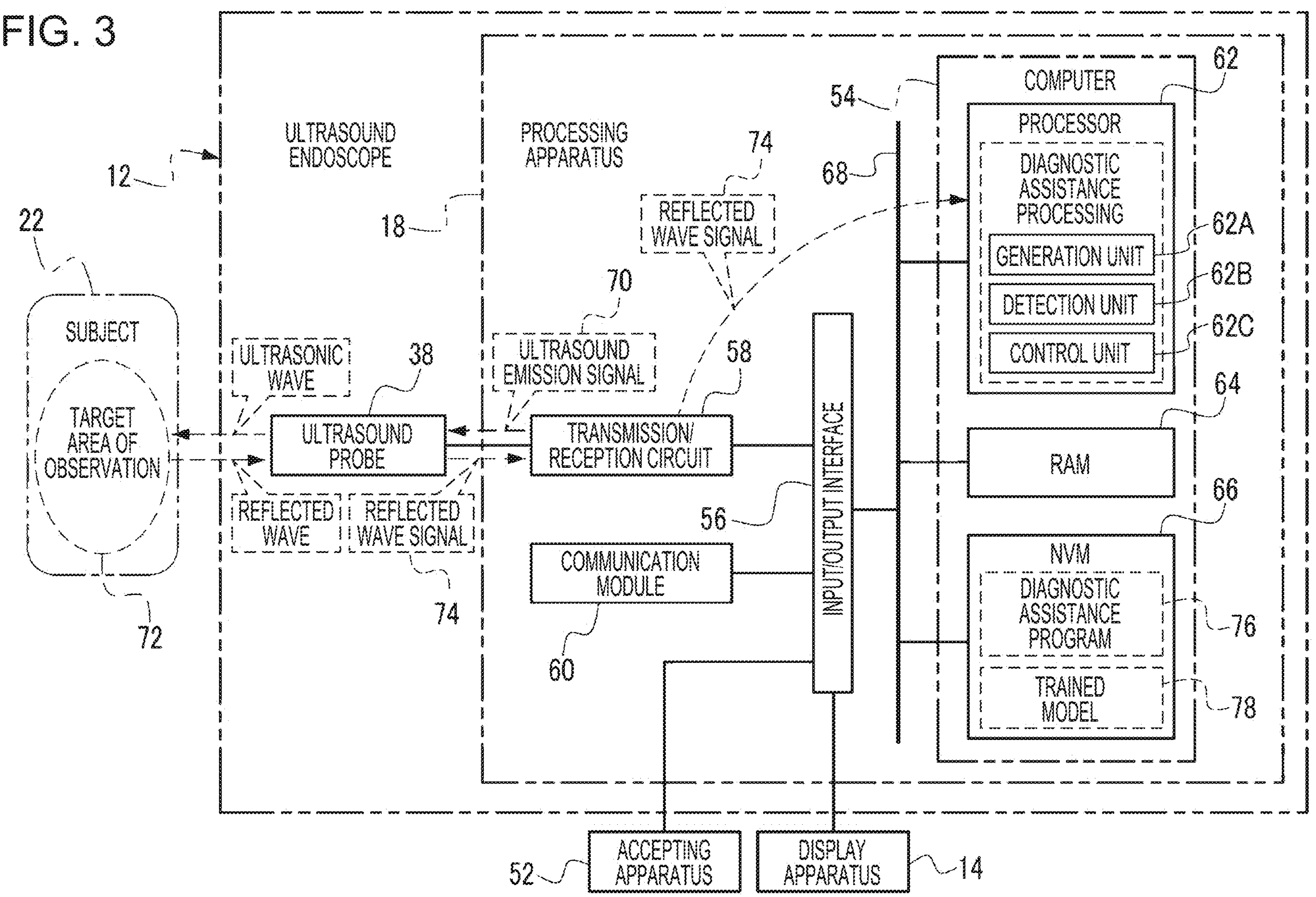
FIG. 3
22
SUBJECT
TARGET AREA OF OBSERVATION
72
12
ULTRASOUND ENDOSCOPE
ULTRASONIC WAVE
38
ULTRASOUND PROBE
REFLECTED WAVE
REFLECTED WAVE SIGNAL
74
18
PROCESSING APPARATUS
74
REFLECTED WAVE SIGNAL
70
ULTRASOUND EMISSION SIGNAL
58
TRANSMISSION/ RECEPTION CIRCUIT
56
COMMUNICATION MODULE
60
INPUT/OUTPUT INTERFACE
54
68
COMPUTER
62
PROCESSOR
DIAGNOSTIC ASSISTANCE PROCESSING
GENERATION UNIT
62A
DETECTION UNIT
62B
CONTROL UNIT
62C
64
RAM
66
NVM
DIAGNOSTIC ASSISTANCE PROGRAM
76
TRAINED MODEL
78
52
ACCEPTING APPARATUS
DISPLAY APPARATUS
14

TRANSMISSION/ RECEPTION CIRCUIT
58
REFLECTED WAVE SIGNAL
74
62A
GENERATION UNIT
B-MODE
GENERATE
REFLECTED WAVE SIGNAL
74
25
24A
DOPPLER MODE
GENERATE
REFLECTED WAVE SIGNAL
74
25
24B1
24B
IMAGE MODE INSTRUCTION
ACCEPTING APPARATUS
52

62C
CONTROL UNIT
FREQUENCY PARAMETER WITHIN FIRST RANGE?
DEPTH PARAMETER WITHIN SECOND RANGE?
BRIGHTNESS PARAMETER WITHIN THIRD RANGE?
DYNAMIC RANGE PARAMETER WITHIN FOURTH RANGE?
SCALE PARAMETER WITHIN FIFTH RANGE?
YES
DETECTION MODE
66
NVM
FREQUENCY PARAMETER
DEPTH PARAMETER
BRIGHTNESS PARAMETER
DYNAMIC RANGE PARAMETER
SCALE PARAMETER
94A (94)
94B (94)
94C (94)
94D (94)
94E (94)

DIAGNOSTIC ASSISTANCE APPARATUS, ULTRASOUND ENDOSCOPE, DIAGNOSTIC ASSISTANCE METHOD, AND PROGRAM

CROSS-REFERENCE TO RELATED APPLICATIONS

This application is a continuation application of International Application No. PCT/JP2023/020699, filed Jun. 2, 2023, the disclosure of which is incorporated herein by reference in its entirety. Further, this application claims priority from Japanese Patent Application No. 2022-105151, filed Jun. 29, 2022, the disclosure of which is incorporated herein by reference in its entirety.

BACKGROUND

1. Technical Field

The technology of the present disclosure relates to a diagnostic assistance apparatus, an ultrasound endoscope, a diagnostic assistance method, and a program.

2. Related Art

WO2020/036121A discloses an endoscope system including: an identification unit that identifies the type of an image captured from a subject; a recognition unit that performs recognition processing to recognize the subject using the image; and a notification unit that provides a notification as to whether or not the recognition processing will function for the specific type of image identified by the identification unit.

JP2021-035442A discloses a diagnostic ultrasound system that provides diagnostic assistance when the image mode is B-mode or CF-mode, but does not provide diagnostic assistance when the image mode is PW-mode.

JP2021-083699A discloses a diagnostic ultrasound apparatus including: a probe that is pressed against the breast and outputs a received signal from the breast via ultrasound transmission and reception; an image generation unit that uses the received signal as a basis for generating an ultrasound image containing a mammary gland image, a pectoral muscle image, and a boundary image in between; an inclination angle computation unit that uses the ultrasound image as a basis for computing an inclination angle of the boundary image; and assistance image generating means that uses the inclination angle of the boundary image as a basis for generating an assistance image to assist with manipulation of the probe.

SUMMARY

One embodiment according to the technology of the present disclosure provides a diagnostic assistance apparatus, an ultrasound endoscope, a diagnostic assistance method, and a program capable of suppressing false positives in which an area other than a specific area is incorrectly detected as the specific area and also capable of avoiding situations in which a visualization of a detection result regarding the specific area interferes with diagnosis.

A first aspect of the technology of the present disclosure is a diagnostic assistance apparatus comprising a processor configured to: acquire a first ultrasound image which is generated by an ultrasound module and which shows a target area of observation; and switch between a first operating mode and a second operating mode according to whether or not reference information referenced to diagnose the target area of observation is combined with the first ultrasound image, according to whether or not the first ultrasound image is an image obtained in an auxiliary image mode, which is an image mode other than a main image mode, or according to a set value that stipulates the image quality of the first ultrasound image, wherein the first operating mode is an operating mode that performs detection of a specific area from the first ultrasound image on the basis of detection assistance information created using a second ultrasound image obtained in the main image mode, and the second operating mode is an operating mode that performs detection of the specific area but does not output a detection result, or that does not perform detection of the specific area.

A second aspect of the technology of the present disclosure is the diagnostic assistance apparatus according to the first aspect, wherein the first operating mode is an operating mode used when the reference information is not combined with the first ultrasound image, and the second operating mode is an operating mode used when the reference information is combined with the first ultrasound image.

A third aspect of the technology of the present disclosure is the diagnostic assistance apparatus according to the first or second aspect, wherein the first operating mode is an operating mode used when the first ultrasound image is not an image obtained in the auxiliary image mode, and the second operating mode is an operating mode used when the first ultrasound image is an image obtained in the auxiliary image mode.

A fourth aspect of the technology of the present disclosure is the diagnostic assistance apparatus according to any one of the first to third aspects, wherein the first operating mode is an operating mode used when the set value is within a specified range, and the second operating mode is an operating mode used when the set value is not within the specified range.

A fifth aspect of the technology of the present disclosure is the diagnostic assistance apparatus according to any one of the first to fourth aspects, wherein the reference information includes color information expressing characteristics in the target area of observation as colors.

A sixth aspect of the technology of the present disclosure is the diagnostic assistance apparatus according to the fifth aspect, wherein the color information includes a plurality of chromatic pixels, the first operating mode is an operating mode used when the number of chromatic pixels having a chroma exceeding a first threshold from among the plurality of chromatic pixels is less than a second threshold, and the second operating mode is an operating mode used when the number is equal to or greater than the second threshold.

A seventh aspect of the technology of the present disclosure is the diagnostic assistance apparatus according to any one of the first to sixth aspects, wherein the reference information includes text information assisting with observation of the target area of observation.

An eighth aspect of the technology of the present disclosure is the diagnostic assistance apparatus according to any one of the first to seventh aspects, wherein the reference information includes a measurement line used for measurement in the target area of observation.

A ninth aspect of the technology of the present disclosure is the diagnostic assistance apparatus according to any one of the first to eighth aspects, wherein the reference information includes treatment assistance information assisting with treatment using fine-needle aspiration.

A 10th aspect of the technology of the present disclosure is the diagnostic assistance apparatus according to any one of the first to ninth aspects, wherein the auxiliary image mode is a first image mode that generates an ultrasound image using a high-frequency component included in a reflected wave obtained when an ultrasonic wave is emitted toward the target area of observation and then reflected by the target area of observation, or a second image mode that combines a B-mode image with a separate image.

An 11th aspect of the technology of the present disclosure is the diagnostic assistance apparatus according to the 10th aspect, wherein the first image mode is THI tissue harmonic imaging) mode, CH (compound harmonic) mode, or CHI (contrast harmonic imaging) mode, and the second image mode is Doppler mode or elastography mode.

A 12th aspect of the technology of the present disclosure is the diagnostic assistance apparatus according to any one of the first to 11th aspects, wherein the set value includes a frequency parameter for adjusting the frequency of an ultrasonic wave emitted from the ultrasound module, a depth parameter for adjusting depth represented in the first ultrasound image, a brightness parameter for adjusting the brightness of the first ultrasound image, a dynamic range parameter for adjusting the dynamic range of the first ultrasound image, and/or a magnification parameter for adjusting the scale of a digital zoom for the first ultrasound image.

A 13th aspect of the technology of the present disclosure is the diagnostic assistance apparatus according to any one of the first to 12th aspects, wherein the ultrasound module has the set value, and the processor is configured to acquire the set value from the ultrasound module.

A 14th aspect of the technology of the present disclosure is the diagnostic assistance apparatus according to any one of the first to 12th aspects, wherein a text image that can be used to identify the set value is combined with a frame containing the first ultrasound image, and the processor is configured to: identify the set value by performing image recognition processing on the text image; and switch between the first operating mode and the second operating mode according to the identified set value.

A 15th aspect of the technology of the present disclosure is the diagnostic assistance apparatus according to any one of the first to 14th aspects, wherein the processor is configured to detect a specific area from the first ultrasound image by an AI (artificial intelligence) approach.

A 16th aspect of the technology of the present disclosure is the diagnostic assistance apparatus according to any one of the first to 15th aspects, wherein the detection assistance information is a trained model obtained by training a model on supervisory data that includes the second ultrasound image.

A 17th aspect of the technology of the present disclosure is the diagnostic assistance apparatus according to any one of the first to 16th aspects, wherein the processor is configured to differentiate a frequency at which to detect the specific area from the first ultrasound image, a precision with which to detect the specific area from the first ultrasound image, and/or a target to be detected as the specific area from the first ultrasound image according to the reference information, the auxiliary image mode, and/or the set value.

An 18th aspect of the technology of the present disclosure is the diagnostic assistance apparatus according to any one of the first to 17th aspects, wherein the ultrasound module is an ultrasound endoscope.

A 19th aspect of the technology of the present disclosure is an ultrasound endoscope comprising: the diagnostic assistance apparatus according to any one of the first to 18th aspects; and an ultrasound endoscope main body to which the ultrasound module is connected.

A 20th aspect of the technology of the present disclosure is a diagnostic assistance method comprising: acquiring a first ultrasound image which is generated by an ultrasound module and which shows a target area of observation; and switching between a first operating mode and a second operating mode according to whether or not reference information referenced to diagnose the target area of observation is combined with the first ultrasound image, according to whether or not the first ultrasound image is an image obtained in an auxiliary image mode, which is an image mode other than a main image mode, or according to a set value that stipulates the image quality of the first ultrasound image, wherein the first operating mode is an operating mode that performs detection of a specific area from the first ultrasound image on the basis of detection assistance information created using a second ultrasound image obtained in the main image mode, and the second operating mode is an operating mode that performs detection of the specific area but does not output a detection result, or that does not perform detection of the specific area.

A 21st aspect of the technology of the present disclosure is a program causing a computer to execute a process comprising: acquiring a first ultrasound image which is generated by an ultrasound module and which shows a target area of observation; and switching between a first operating mode and a second operating mode according to whether or not reference information referenced to diagnose the target area of observation is combined with the first ultrasound image, according to whether or not the first ultrasound image is an image obtained in an auxiliary image mode, which is an image mode other than a main image mode, or according to a set value that stipulates the image quality of the first ultrasound image, wherein the first operating mode is an operating mode that performs detection of a specific area from the first ultrasound image on the basis of detection assistance information created using a second ultrasound image obtained in the main image mode, and the second operating mode is an operating mode that performs detection of the specific area but does not output a detection result, or that does not perform detection of the specific area.

BRIEF DESCRIPTION

Exemplary embodiments according to the technique of the present disclosure will be described in detail based on the following figures, wherein:

FIG. 3 is a block diagram illustrating an example of a configuration of an ultrasound endoscope;

FIG. 11 is a conceptual diagram illustrating an example of details of processing by a generation unit and a control unit according to a second modification;

FIG. 12 is a flowchart illustrating an example of the flow of diagnostic assistance processing according to a second modification;

DETAILED DESCRIPTION

The following describes, in accordance with the attached drawings, examples of embodiments of a diagnostic assistance apparatus, an ultrasound endoscope, a diagnostic assistance method, and a program according to the technology of the present disclosure.

First, terms used in the following description will be explained.

CPU is an abbreviation for "central processing unit". GPU is an abbreviation for "graphics processing unit". TPU is an abbreviation for "tensor processing unit". RAM is an abbreviation for "random access memory". NVM is an abbreviation for "non-volatile memory". EEPROM is an abbreviation for "electrically erasable programmable read-only memory". ASIC is an abbreviation for "application-specific integrated circuit". PLD is an abbreviation for "programmable logic device". FPGA is an abbreviation for "field-programmable gate array". SoC is an abbreviation for "system-on-a-chip". SSD is an abbreviation for "solid-state drive". USB is an abbreviation for "Universal Serial Bus". HDD is an abbreviation for "hard disk drive". EL is an abbreviation for "electroluminescence". CMOS is an abbreviation for "complementary metal-oxide-semiconductor". CCD is an abbreviation for "charge-coupled device". PC is an abbreviation for "personal computer". LAN is an abbreviation for "local area network". WAN is an abbreviation for "wide area network". AI is an abbreviation for "artificial intelligence". BLI is an abbreviation for "blue light imaging". LCI is an abbreviation for "linked color imaging". NN is an abbreviation for "neural network". CNN is an abbreviation for "convolutional neural network". R-CNN is an abbreviation for "region-based convolutional neural network". YOLO is an abbreviation for "you only look once". RNN is an abbreviation for "recurrent neural network". FCN is an abbreviation for "fully convolutional network". THI is an abbreviation for "tissue harmonic imaging". CH is an abbreviation for "compound harmonic". CHI is an abbreviation for "contrast harmonic imaging".

Figure 1:
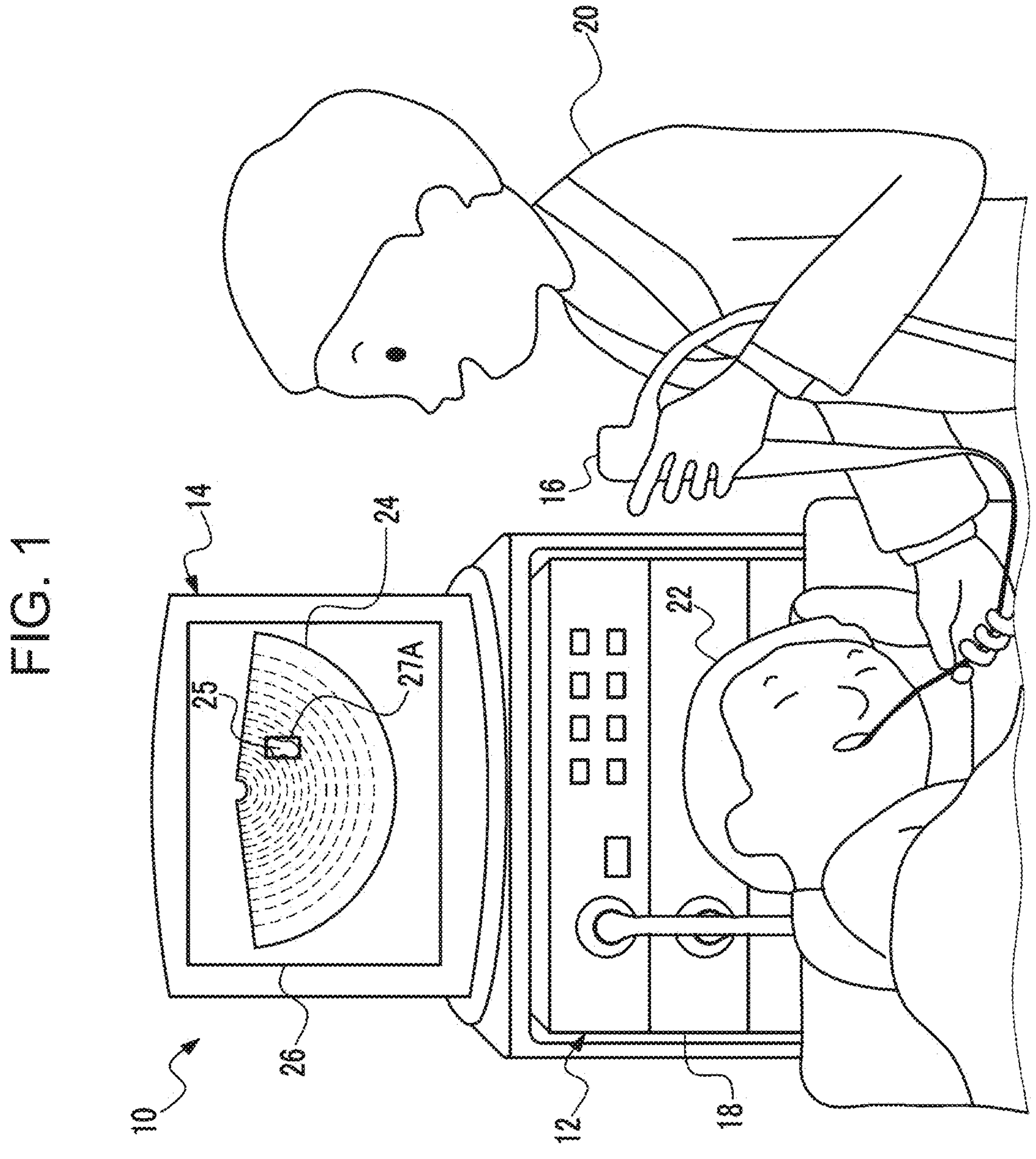
FIG. 1 is a conceptual diagram illustrating an example of an aspect in which an endoscope system is used.

As illustrated by way of example in FIG. 1, an endoscope system 10 is provided with an ultrasound endoscope 12 and a display apparatus 14. The ultrasound endoscope 12 is an ultrasound endoscope of the convex type, and is provided with an ultrasound endoscope main body 16 and a processing apparatus 18. The ultrasound endoscope 12 is an example of an "ultrasound module" and an "ultrasound endoscope" according to the technology of the present disclosure. The processing apparatus 18 is an example of a "diagnostic assistance apparatus" according to the technology of the present disclosure. The ultrasound endoscope main body 16 is an example of an "ultrasound endoscope main body" according to the technology of the present disclosure.

Note that although the present embodiment gives an ultrasound endoscope of the convex type as an example of the ultrasound endoscope 12, this is merely one example, and the technology of the present disclosure is also achieved with an ultrasound endoscope of the radial type.

The ultrasound endoscope main body 16 is used by a physician 20, for example. The processing apparatus 18 is connected to the ultrasound endoscope main body 16 and exchanges various signals with the ultrasound endoscope main body 16. That is, the processing apparatus 18 may output a signal to the ultrasound endoscope main body 16 to control operations by the ultrasound endoscope main body 16, and perform various types of signal processing on a signal inputted from the ultrasound endoscope main body 16.

The ultrasound endoscope 12 is an apparatus for providing medical care (for example, diagnosis and/or treatment) with respect to a target site of care (for example, an organ such as the pancreas) inside the body of a subject 22, and generates and outputs an ultrasound image 24 indicating a target area of observation that includes the target site of care.

For example, in the case of observing a target area of observation inside the body of the subject 22, the physician 20 inserts the ultrasound endoscope main body 16 into the body of the subject 22 from the mouth or nose (in the example illustrated in FIG. 1, the mouth), and emits an ultrasonic wave at the position of the stomach, duodenum, or the like. The ultrasound endoscope main body 16 emits an ultrasonic wave toward the target area of observation inside the body of the subject 22 and detects a reflected wave obtained when the emitted ultrasonic wave is reflected by the target area of observation.

Note that although the example in FIG. 1 illustrates a situation in which upper gastrointestinal endoscopy is performed, the technology of the present disclosure is not limited thereto, and the technology of the present disclosure is also applicable to lower gastrointestinal endoscopy, bronchoscopy, or the like.

The processing apparatus 18 generates the ultrasound image 24 on the basis of the reflected wave detected by the ultrasound endoscope main body 16, and outputs the generated ultrasound image 24 to the display apparatus 14 or the like.

The display apparatus 14 displays various information, including images, under control by the processing apparatus 18. The display apparatus 14 may be a liquid crystal display or an EL display, for example. The ultrasound image 24 generated by the processing apparatus 18 is displayed as a dynamic image on a screen 26 of the display apparatus 14. The example in FIG. 1 illustrates a situation in which the ultrasound image 24 on the screen 26 contains a lesion area 25, which indicates a spot corresponding to a lesion. Also, although details will be described later, in the example illustrated in FIG. 1, a rectangular detection frame 27A that can be used to identify the position of the lesion area 25 in the ultrasound image 24 is displayed on the screen 26.

The physician 20 observes the ultrasound image 24 displayed on the screen 26 to assess whether or not a lesion is shown in the target area of observation, and if a lesion is discovered, the physician 20 refers to the detection frame 27A in the ultrasound image 24 to identify the position of the lesion inside the target area of observation.

Note that although the example in FIG. 1 illustrates an example arrangement in which the ultrasound image 24 is displayed on the screen 26 of the display apparatus 14, this is merely one example, and the ultrasound image 24 may also be displayed on a display apparatus (for example, the display of a tablet terminal) other than the display apparatus 14. The ultrasound image 24 may also be stored in a non-transitory computer readable medium (for example, flash memory, an HDD, and/or magnetic tape).

The ultrasound image 24 is displayed on the display apparatus 14 in accordance with an image mode selected by the physician 20. An image mode refers to a display mode by which to convert a reflected wave detected by the ultrasound endoscope main body 16 into an image for display on the display apparatus 14. In the present embodiment, there are two image modes that may be selected by the physician 20: brightness mode (B-mode) and Doppler mode. B-mode is an example of a "main image mode" according to the technology of the present disclosure, and Doppler mode is an example of an "auxiliary image mode, which is an image mode other than the main image mode" according to the technology of the present disclosure.

B-mode is an image mode in which the intensity of the reflected wave is converted into luminance and displayed as a two-dimensional tomographic image (hereinafter referred to as a "B-mode image"). Doppler mode is an image mode in which hemodynamics identified using the Doppler effect are superimposed onto a B-mode image as color information. In the following, "Doppler image" is used to refer to an image generated under Doppler mode, that is, an image obtained by superimposing color information indicating hemodynamics onto a B-mode image. In the following, images generated under different image modes, such as B-mode images, Doppler images, and the like, are simply referred to as the "ultrasound image 24" out of convenience when it is not necessary to distinguish between such images.

The ultrasound image 24 is a dynamic image including multiple frames generated in accordance with a frame rate stipulated according to the image mode. The frame rate of Doppler mode is lower than the frame rate of B-mode. Note that although a dynamic image is given by way of example herein, this is merely one example, and the technology of the present disclosure is also achieved when the ultrasound image 24 is a still image.

Figure 2:
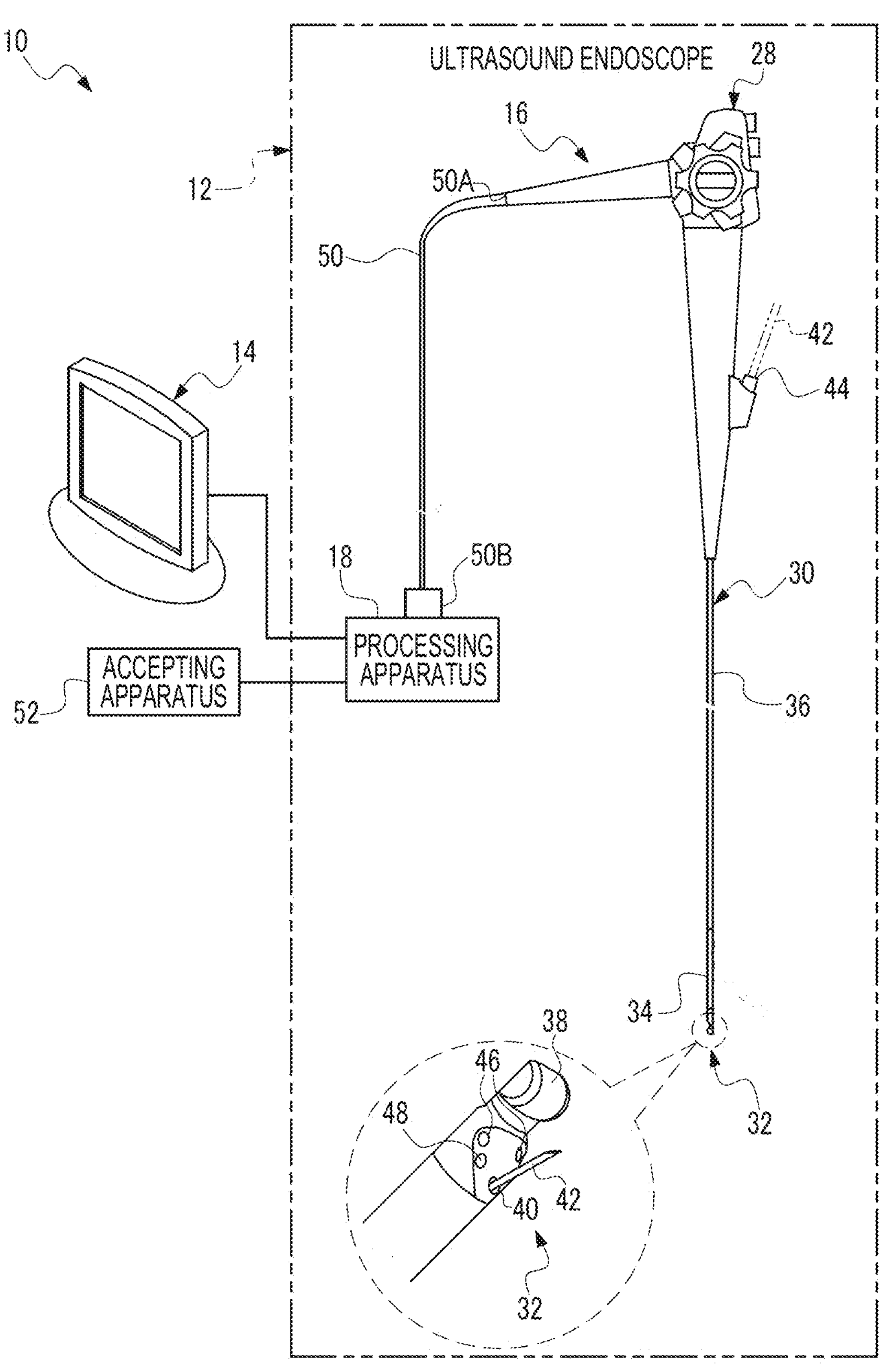
FIG. 2 is a conceptual diagram illustrating an example of an overall configuration of an endoscope system.

As illustrated by way of example in FIG. 2, the ultrasound endoscope main body 16 is provided with a manipulation part 28 and an insertion part 30. The insertion part 30 is formed into a tubular shape. The insertion part 30 has a leading end part 32, a curving part 34, and a flexible part 36. The leading end part 32, the curving part 34, and the flexible part 36 are disposed from the leading-end side to the base-end side of the insertion part 30 in the order of the leading end part 32, the curving part 34, and the flexible part 36. The flexible part 36 is formed from a long, flexible material, and connects the manipulation part 28 with the curving part 34. Manipulating the manipulation part 28 causes the curving part 34 to partially curve or rotate about the axis of the insertion part 30. As a result, the insertion part 30 is fed deeper into a luminal organ while curving or rotating about the axis of the insertion part 30 according to the shape of a luminal organ (the shape of the duodenum tract, for example).

An ultrasound probe 38 and a treatment tool aperture 40 are provided in the leading end part 32. The ultrasound probe 38 is provided on the leading-end side of the leading end part 32. The ultrasound probe 38 is an ultrasound probe of the convex type that emits an ultrasonic wave and receives a reflected wave obtained when the emitted ultrasonic wave is reflected by the target area of observation.

The treatment tool aperture 40 is formed closer to the base-end side of the leading end part 32 than the ultrasound probe 38. The treatment tool aperture 40 is an aperture for allowing a treatment tool 42 to protrude from the leading end part 32. A treatment tool insertion port 44 is formed in the manipulation part 28, and the treatment tool 42 is inserted into the insertion part 30 from the treatment tool insertion port 44. The treatment tool 42 passes through the interior of the insertion part 30 to protrude out of the ultrasound endoscope main body 16 from the treatment tool aperture 40. The treatment tool aperture 40 also functions as an aspiration port to aspirate blood, internal contaminants, and the like.

In the example illustrated in FIG. 2, a puncture needle is illustrated as the treatment tool 42. Note that this is merely one example, and the treatment tool 42 may also be grasping forceps and/or a sheath.

In the example illustrated in FIG. 2, an illumination apparatus 46 and a camera 48 are provided in the leading end part 32. The illumination apparatus 46 radiates light. The type of light radiated from the illumination apparatus 46 may be visible light (white light, for example), non-visible light (near-infrared light, for example), and/or special light, for example. The special light may be light for BLI and/or light for LCI, for example.

The camera 48 images the inside of a luminal organ using an optical method. One example of the camera 48 is a CMOS camera. A CMOS camera is merely one example, and the camera 48 may also be another type of camera, such as a CCD camera. Note that an image obtained through imaging by the camera 48 is displayed on the display apparatus 14, displayed on a display apparatus (for example, the display of a tablet terminal) other than the display apparatus 14, and/or stored in a storage medium (for example, flash memory, an HDD, and/or magnetic tape).

The ultrasound endoscope 12 is provided with a processing apparatus 18 and a universal cord 50. The universal cord 50 has a base end part 50A and a leading end part 50B. The base end part 50A is connected to the manipulation part 28. The leading end part 50B is connected to the processing apparatus 18. That is, the ultrasound endoscope main body 16 and the processing apparatus 18 are connected via the universal cord 50.

The endoscope system 10 is provided with an accepting apparatus 52. The accepting apparatus 52 is connected to the processing apparatus 18. The accepting apparatus 52 accepts instructions from a user. Examples of the accepting apparatus 52 include: an operation panel with multiple hardware keys and/or a touch panel; a keyboard; a mouse; a trackball; a footswitch; a smart device; and/or a microphone.

The processing apparatus 18 performs various types of signal processing and exchanges various signals with the ultrasound endoscope main body 16, according to instructions accepted by the accepting apparatus 52. For example, according to an instruction accepted by the accepting apparatus 52, the processing apparatus 18 causes the ultrasound probe 38 to emit an ultrasonic wave, and generates and outputs the ultrasound image 24 (see FIG. 1) on the basis of a reflected wave received by the ultrasound probe 38.

The display apparatus 14 is also connected to the processing apparatus 18. The processing apparatus 18 controls the display apparatus 14 according to instructions accepted by the accepting apparatus 52. This causes, for example, the ultrasound image 24 generated by the processing apparatus 18 to be displayed on the screen 26 of the display apparatus 14 (see FIG. 1).

As illustrated by way of example in FIG. 3, the processing apparatus 18 is provided with a computer 54, an input/output interface 56, a transmission/reception circuit 58, and a communication module 60. The computer 54 is an example of a "computer" according to the technology of the present disclosure.

The computer 54 is provided with a processor 62, RAM 64, and NVM 66. The input/output interface 56, processor 62, RAM 64, and NVM 66 are connected to a bus 68.

The processor 62 controls the processing apparatus 18 overall. For example, the processor 62 includes a CPU and a GPU, and the GPU operates under control by the CPU and is mainly responsible for executing image processing. Note that the processor 62 may also be one or more CPUs with integrated GPU functionality, or one or more CPUs without integrated GPU functionality. The processor 62 may also include a multi-core CPU, and may also include a TPU. The processor 62 is an example of a "processor" according to the technology of the present disclosure.

The RAM 64 is a memory in which information is stored temporarily, and is used as work memory by the processor 62. The NVM 66 is a non-volatile storage apparatus storing various programs, various parameters, and the like. The NVM 66 may be flash memory (EEPROM, for example) and/or an SSD, for example. Note that flash memory and an SSD are merely one example, and the NVM 66 may also be another type of non-volatile storage apparatus, such as an HDD, and may also be a combination of two or more types of non-volatile storage apparatuses.

The accepting apparatus 52 is connected to the input/output interface 56, and the processor 62 acquires an instruction accepted by the accepting apparatus 52 via the input/output interface 56 and executes processing according to the acquired instruction.

The transmission/reception circuit 58 is connected to the input/output interface 56. The transmission/reception circuit 58 generates an ultrasound emission signal 70 with a pulse waveform according to an instruction from the processor 62, and outputs the generated ultrasound emission signal 70 to the ultrasound probe 38. The ultrasound probe 38 converts the ultrasound emission signal 70 inputted from the transmission/reception circuit 58 into an ultrasonic wave and emits the ultrasonic wave toward a target area of observation 72 of the subject 22. The ultrasound probe 38 receives a reflected wave obtained when the ultrasonic wave emitted from the ultrasound probe 38 is reflected by the target area of observation 72, converts the reflected wave into a reflected wave signal 74, which is an electrical signal, and outputs the reflected wave signal 74 to the transmission/reception circuit 58. The transmission/reception circuit 58 digitizes the reflected wave signal 74 inputted from the ultrasound probe 38 and outputs the digitized reflected wave signal 74 to the processor 62 via the input/output interface 56. The processor 62 generates the ultrasound image 24 (see FIG. 1) illustrating the state of the target area of observation 72 on the basis of the reflected wave signal 74 inputted from the transmission/reception circuit 58 via the input/output interface 56.

Although omitted from illustration in FIG. 3, the illumination apparatus 46 (see FIG. 2) is also connected to the input/output interface 56. The processor 62 controls the illumination apparatus 46 via the input/output interface 56 to change the type of light radiated from the illumination apparatus 46 and to adjust the light intensity. Although omitted from illustration in FIG. 3, the camera 48 (see FIG. 2) is also connected to the input/output interface 56. The processor 62 controls the camera 48 via the input/output interface 56 and acquires, via the input/output interface 56, an image obtained by having the camera 48 image the inside of the body of the subject 22.

The communication module 60 is connected to the input/output interface 56. The communication module 60 is an interface including a communication processor, an antenna, and the like. The communication module 60 is connected to a LAN, WAN, or other network (not illustrated), and directs communication between the processor 62 and an external apparatus.

The display apparatus 14 is connected to the input/output interface 56, and the processor 62 controls the display apparatus 14 via the input/output interface 56, thereby causing the display apparatus 14 to display various information.

The accepting apparatus 52 is connected to the input/output interface 56, and the processor 62 acquires an instruction accepted by the accepting apparatus 52 via the input/output interface 56 and executes processing according to the acquired instruction.

A diagnostic assistance program 76 and a trained model 78 are stored in the NVM 66. The processor 62 performs diagnostic assistance processing by reading out the diagnostic assistance program 76 from the NVM 66 and executing the read diagnostic assistance program 76 in the RAM 64. The diagnostic assistance processing is processing to detect a lesion from the target area of observation 72 by an AI approach, and assist the physician 20 (see FIG. 1) with diagnosis on the basis of the detection result.

The processor 62 performs the diagnostic assistance processing to detect a lesion from the target area of observation 72 by detecting a spot corresponding to a lesion from the ultrasound image 24 (see FIG. 1) according to the trained model 78. The diagnostic assistance processing is realized by the processor 62 operating as a generation unit 62A, a detection unit 62B, and a control unit 62C according to the diagnostic assistance program 76 executed in the RAM 64.

Note that the diagnostic assistance program 76 is an example of a "program" according to the technology of the present disclosure. The trained model 78 is a trained model having a data structure to be used in processing to detect a lesion from the ultrasound image 24. The trained model 78 is an example of "detection assistance information" and a "trained model" according to the technology of the present disclosure.

Figure 4:
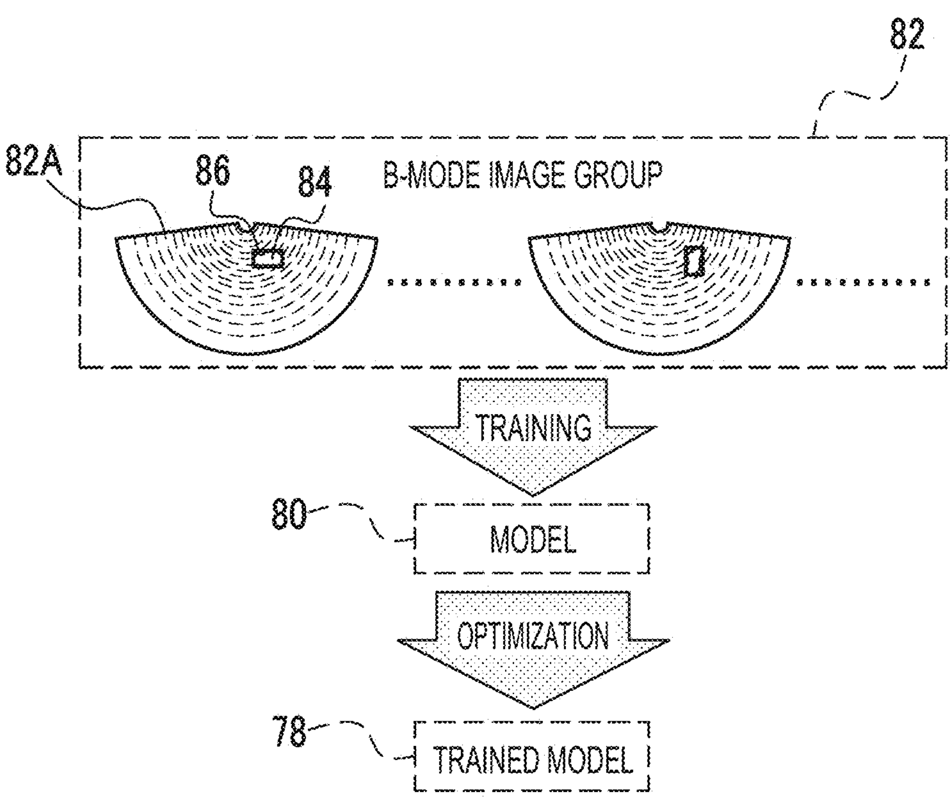
FIG. 4 is a conceptual diagram illustrating an example of an aspect in which a trained model is generated by training a model on a B-mode image group.

As illustrated by way of example in FIG. 4, the trained model 78 is generated by training an untrained model 80. To train the model 80, a B-mode image group 82 is used as supervisory data. The B-mode image group 82 contains multiple different B-mode images 82A. The B-mode image 82A is an example of a "second ultrasound image" according to the technology of the present disclosure. The B-mode image group 82 is an example of "supervisory data" according to the technology of the present disclosure.

The model 80 may be a mathematical model using a NN, for example. The type of the NN may be YOLO, an R-CNN, or an FCN, for example. The NN used for the model 80 may also be an RNN combined with YOLO, an R-CNN, or an FCN. RNNs are suitable for learning multiple images obtained in a time series. Note that the types of NN given here are merely one example, and another type of NN enabling object detection by learning images may also be used.

Lesions are shown in the multiple B-mode images 82A. That is, each B-mode image 82A has a lesion area 84, which is a spot that corresponds to a lesion. An annotation 86 is attached to each B-mode image 82A. The annotation 86 is information that can be used to identify the position of the lesion area 84 in the B-mode image 82A (for example, information including multiple coordinates that can be used to identify the position of a rectangular frame bounding the lesion area 84).

For convenience, information that can be used to identify the position of the lesion area 84 in the B-mode image 82A is given as an example of the annotation 86, but this is merely one example. For example, the annotation 86 may also including other types of information for identifying a lesion shown in the B-mode image 82A, such as information that can be used to identify the type of lesion shown in the B-mode image 82A.

Note that for convenience, the following describes processing using the trained model 78 as processing that is actively performed by the trained model 78. In other words, for convenience, the trained model 78 is regarded as a function that processes inputted information and outputs a processing result. Additionally, for convenience, the following also describes a portion of the processing for training the model 80 as processing that is actively performed by the model 80. In other words, for convenience, the model 80 is regarded as a function that processes inputted information and outputs a processing result.

The B-mode images 82A included in the B-mode image group 82 are inputted into the model 80. In response, the model 80 predicts the position of the lesion area 84 from the inputted B-mode images 82A and outputs a prediction result. The prediction result includes information that can be used to identify the position predicted by the model 80 as the position of the lesion area 84 in the B-mode images 82A. The information that can be used to identify the position predicted by the model 80 may be, for example, information including multiple coordinates that can be used to identify the position of a bounding box surrounding the area predicted as the position where the lesion area 84 is present (that is, the position of a bounding box within the B-mode image 82A).

Adjustments are made to the model 80 according to the error between the annotation 86 attached to the B-mode image 82A inputted into the model 80 and the prediction result outputted from the model 80. That is, the model 80 is optimized by adjusting multiple optimization variables within the model 80 (for example, multiple connection weights and multiple offset values) such that the error is minimized, thereby generating the trained model 78. In other words, the data structure of the trained model 78 is obtained by training the model 80 on multiple different B-mode images 82A with annotations 86 attached.

In this way, the trained model 78 is a mathematical model generated by training the model 80 on the B-mode image group 82. For this reason, the trained model 78 can be used effectively to detect the lesion area 25 (see FIG. 1) from a B-mode image generated as the ultrasound image 24, for example, but in the case of detecting the lesion area 25 from a Doppler image generated as the ultrasound image 24, there is an increased likelihood of false positives compared to B-mode images. This is because the model 80 has not learned the color information included in Doppler images. Also, if it is assumed that the lesion area 25 is detected from a Doppler image and the detection frame 27A (see FIG. 1) is displayed within the Doppler image as a detection result, the color information included in the Doppler image (that is, colorized information indicating hemodynamics) and the detection frame 27A will be visualized in a mixed state, and for the physician 20, the presence of the detection frame 27A may interfere with diagnosis.

Accordingly, in the processing apparatus 18 according to the present embodiment, diagnostic assistance processing is performed, as illustrated by way of example in FIGS. 5 to 9B. Hereinafter, an example of the diagnostic assistance processing will be described specifically.

Figure 5:
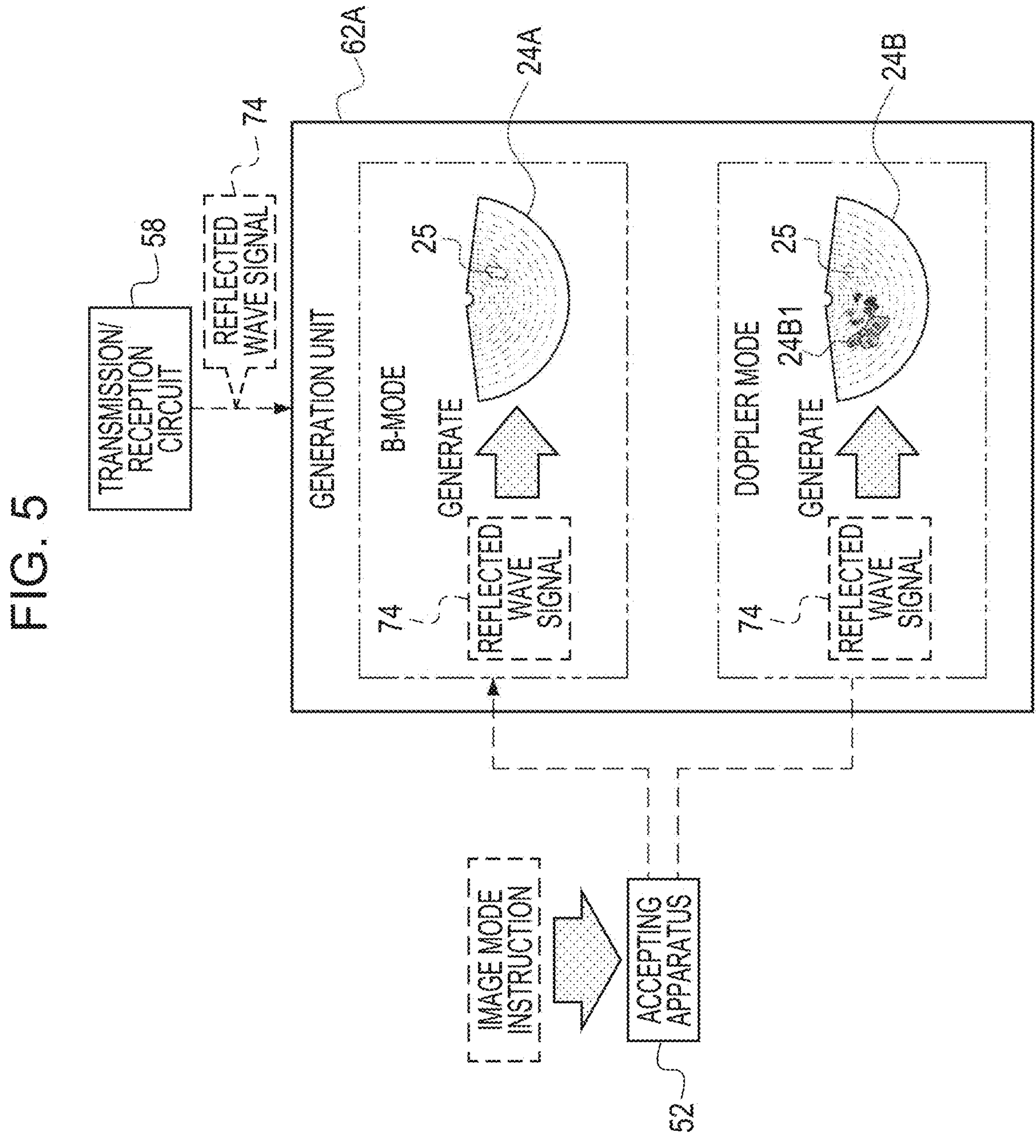
FIG. 5 is a conceptual diagram illustrating an example of details of processing by a generation unit.

As illustrated by way of example in FIG. 5, when the accepting apparatus 52 accepts an instruction (hereinafter referred to as an "image mode instruction") selecting a type of image mode (herein, B-mode or Doppler mode as an example), the generation unit 62A sets B-mode or Doppler mode according to the image mode instruction. In the present embodiment, B-mode is used as a main image mode by the physician 20, and Doppler mode is used as a sub image mode (that is, an auxiliary image mode) by the physician 20.

In B-mode, the generation unit 62A acquires the reflected wave signal 74 from the transmission/reception circuit 58, and acquires a B-mode image 24A by generating the B-mode image 24A on the basis of the acquired reflected wave signal 74. The target area of observation 72 is shown in the B-mode image 24A. That is, the B-mode image 24A is an image that two-dimensionally illustrates a tomographic section of the target area of observation 72. In the example illustrated in FIG. 5, a B-mode image 24A with the lesion area 25 is generated by the generation unit 62A, but obviously a B-mode image 24A not showing a lesion may also be generated by the generation unit 62A. The B-mode image 24A is an example of a "first ultrasound image" according to the technology of the present disclosure. The lesion area 25 is an example of a "specific area" according to the technology of the present disclosure.

In Doppler mode, the generation unit 62A acquires the reflected wave signal 74 from the transmission/reception circuit 58 and generates a Doppler image 24B on the basis of the acquired reflected wave signal 74. The Doppler image 24B is an image obtained by superimposing color information 24B1 representing characteristics in the target area of observation 72 (see FIG. 3) as colors (that is, chromatic colors) onto the B-mode image 24A. For example, the color information 24B1 is information indicating hemodynamics identified using the Doppler effect. The color information 24B1 is information that the physician 20 refers to in order to diagnose the target area of observation 72 (see FIG. 3).

Note that the Doppler image 24B is an example of an "image obtained in an auxiliary image mode" according to the technology of the present disclosure. The color information 24B1 is an example of "reference information", "color information", and a "separate image" according to the technology of the present disclosure. The superimposing of the color information 24B1 onto the B-mode image 24A is an example of "combining" according to the technology of the present disclosure.

Figure 6:
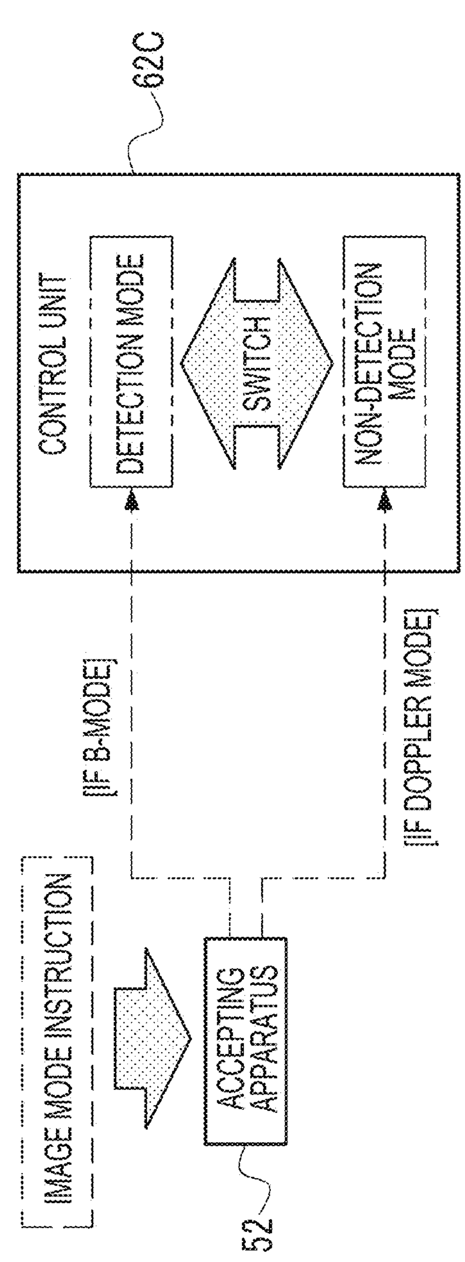
FIG. 6 is a conceptual diagram illustrating an example of details of processing for switching between a detection mode and a non-detection mode.

As illustrated by way of example in FIG. 6, the control unit 62C switches between a detection mode and a non-detection mode according to whether the ultrasound image 24 generated by the generation unit 62A is the B-mode image 24A or the Doppler image 24B. In the present embodiment, the control unit 62C determines whether the ultrasound image 24 generated by the generation unit 62A is the B-mode image 24A or the Doppler image 24B according to the image mode instruction accepted by the accepting apparatus 52, and switches between detection mode and non-detection mode according to the determination result. That is, the control unit 62C switches between detection mode and non-detection mode according to the image mode set in accordance with the image mode instruction accepted by the accepting apparatus. For example, the control unit 62C sets detection mode in the case of B-mode and sets non-detection mode in the case of Doppler mode.

Detection mode is an operating mode to detect the lesion area 25 (see FIG. 5) from the B-mode image 24A (see FIG. 5) by an AI approach, or in other words, an operating mode to detect the lesion area 25 from the B-mode image 24A on the basis of the trained model 78 created using the B-mode image group 82. Detection mode is used when the color information 24B1 is not superimposed onto the B-mode image 24A. In other words, detection mode is used when the Doppler image 24B is not generated by the generation unit 62A (that is, when the B-mode image 24A is generated by the generation unit 62A).

Non-detection mode is an operating mode that does not perform detection of the lesion area 25 from the ultrasound image 24. Herein, an operating mode that does not perform detection of the lesion area 25 from the ultrasound image 24 is given as an example of non-detection mode, but the technology of the present disclosure is not limited thereto. For example, non-detection mode may also be an operating mode that performs detection of the lesion area 25 from the ultrasound image 24 but does not output a detection result (in other words, an operating mode in which the detection of the lesion area 25 by an AI approach is performed in the background, but a detection result is not visualized). Non-detection mode is used when the color information 24B1 is superimposed onto the B-mode image 24A. In other words, non-detection mode is used when the Doppler image 24B is generated by the generation unit 62A.

Figure 7:
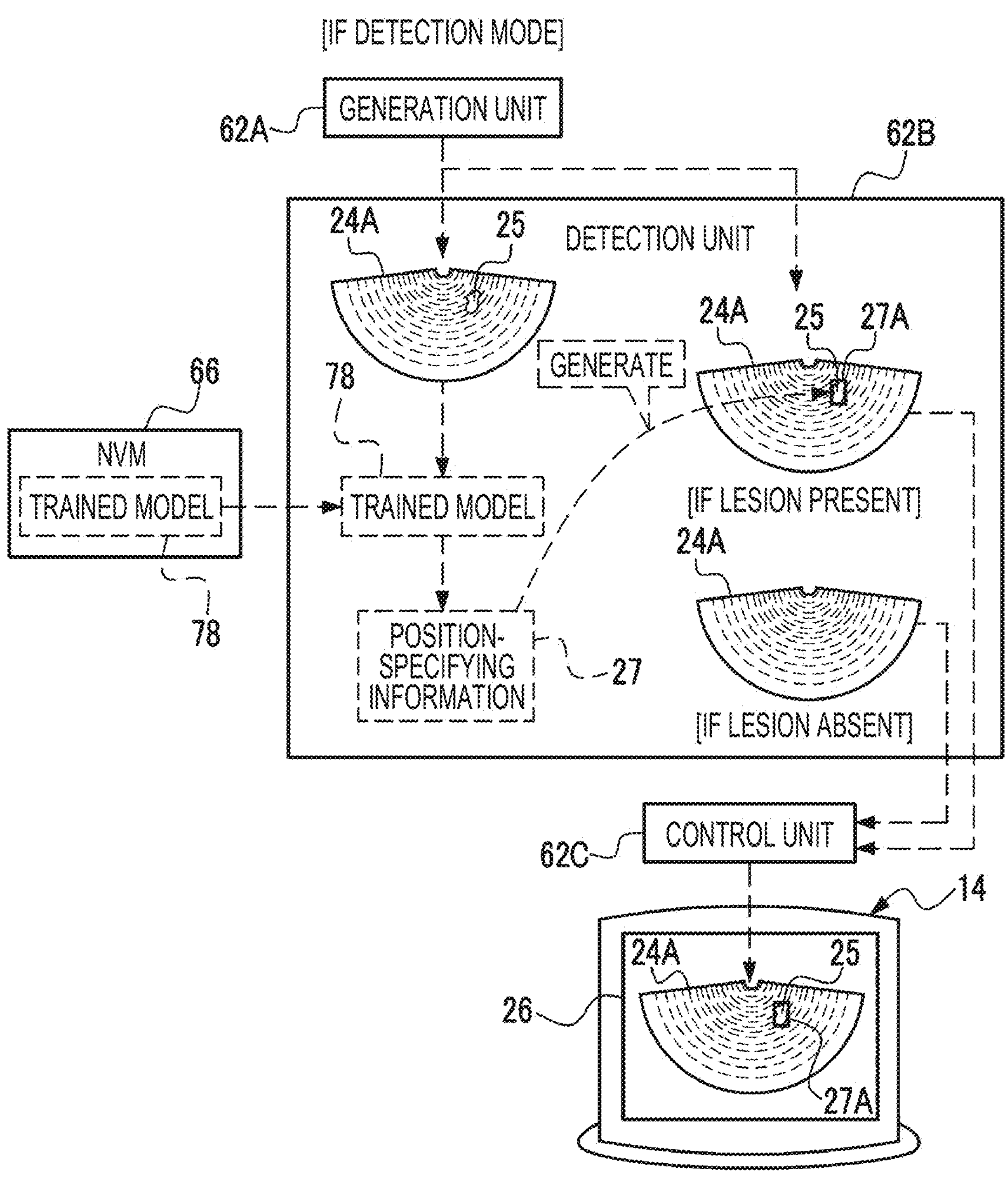
FIG. 7 is a conceptual diagram illustrating an example of details of processing to detect a lesion area from a B-mode image and display the B-mode image on a screen of a display apparatus.

As illustrated by way of example in FIG. 7, in the case of detection mode, the detection unit 62B detects, according to the trained model 78, a lesion from the B-mode image 24A generated by the generation unit 62A. That is, the detection unit 62B determines the presence or absence of the lesion area 25 in the B-mode image 24A according to the trained model 78, and if the lesion area 25 is present in the B-mode image 24A, the detection unit 62B generates position-specifying information 27 (for example, information including multiple coordinates identifying the position of the lesion area 25). The processing by which the detection unit 62B detects a lesion is described as being performed by the trained model 78 as follows: the trained model 78, upon accepting the input of the B-mode image 24A generated by the generation unit 62A, determines the presence or absence of the lesion area 25 in the inputted B-mode image 24A. If the lesion area 25 is determined to be present in the B-mode image 24A (that is, if a lesion shown in the B-mode image 24A is detected), the trained model 78 outputs position-specifying information 27. The detection frame 27A is a rectangular frame corresponding to a bounding box (for example, the bounding box with the highest confidence score) used when the trained model 78 detects the lesion area 25 from the B-mode image 24A. That is, the detection frame 27A is a frame surrounding the lesion area 25 detected by the trained model 78.

The detection unit 62B, following the position-specifying information 27, attaches the detection frame 27A to the B-mode image 24A corresponding to the position-specifying information 27 outputted from the trained model 78 (that is, the B-mode image 24A that was inputted into the trained model 78 in order to output the position-specifying information 27). That is, the detection unit 62B superimposes the detection frame 27A onto the B-mode image 24A corresponding to the position-specifying information 27 outputted from the trained model 78 so as to surround the lesion area 25, thereby attaching the detection frame 27A to the B-mode image 24A. If the trained model 78 determines that the lesion area 25 is present in the B-mode image 24A, the detection unit 62B outputs the B-mode image 24A with an attached detection frame 27A to the control unit 62C. If the trained model 78 determines that the lesion area 25 is not present in the B-mode image 24A, the detection unit 62B outputs the B-mode image 24A without an attached detection frame 27A to the control unit 62C.

The control unit 62C displays the B-mode image 24A inputted from the detection unit 62B (that is, the B-mode image 24A reflecting the result of the detection by the detection unit 62B) on the screen 26 of the display apparatus 14. If a lesion is shown in the B-mode image 24A, the B-mode image 24A with an attached detection frame 27A surrounding the lesion area 25 (that is, the B-mode image 24A with the detection frame 27A superimposed) is displayed on the screen 26. On the other hand, if a lesion is not shown in the B-mode image 24A, the B-mode image 24A without an attached detection frame 27A (that is, the B-mode image 24A outputted from the trained model 78) is displayed on the screen 26.

Figure 8:
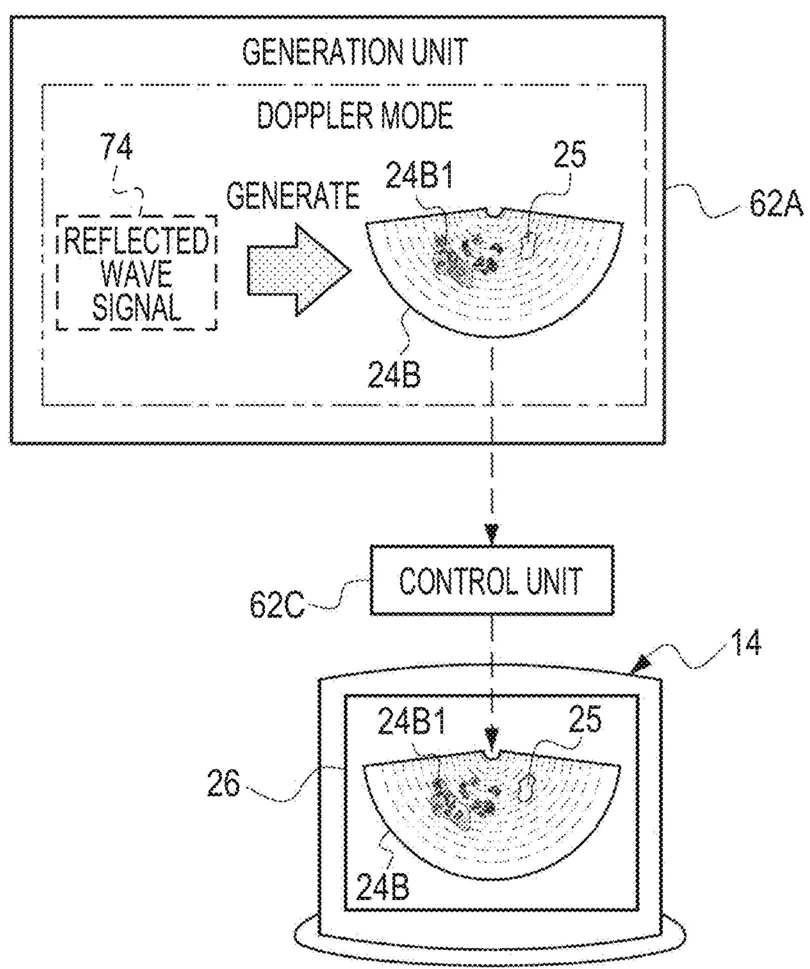
FIG. 8 is a conceptual diagram illustrating an example of details of processing to generate and display a Doppler image on a screen of a display apparatus.

As illustrated by way of example in FIG. 8, in the case of non-detection mode, the control unit 62C acquires the Doppler image 24B generated by the generation unit 62A and displays the acquired Doppler image 24B on the screen 26 of the display apparatus 14.

Next, the operation of the endoscope system 10 will be described with reference to FIGS. 9A and 9B.

Figure 9A:
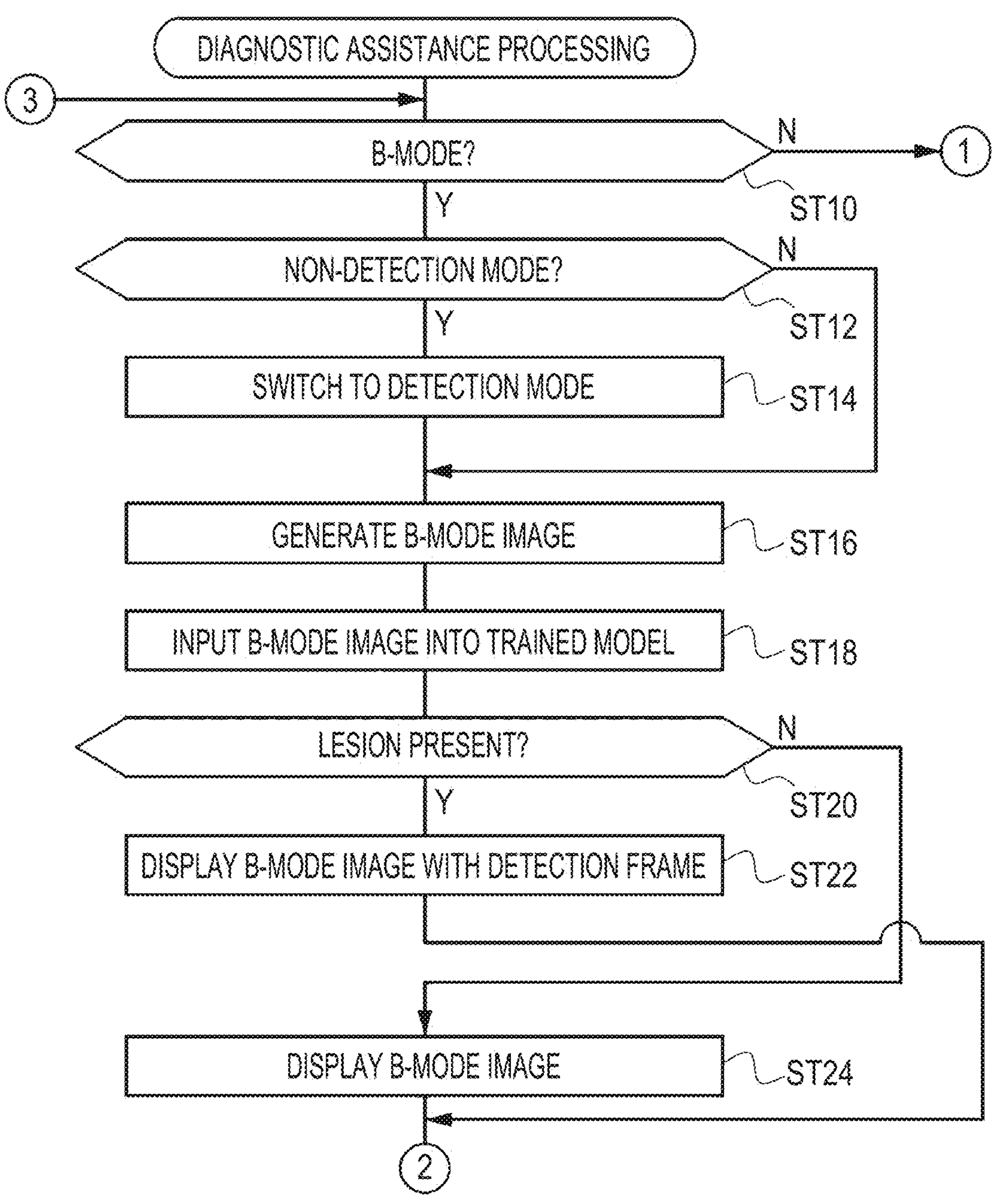
FIG. 9A is a flowchart illustrating an example of the flow of diagnostic assistance processing.
Figure 9B:
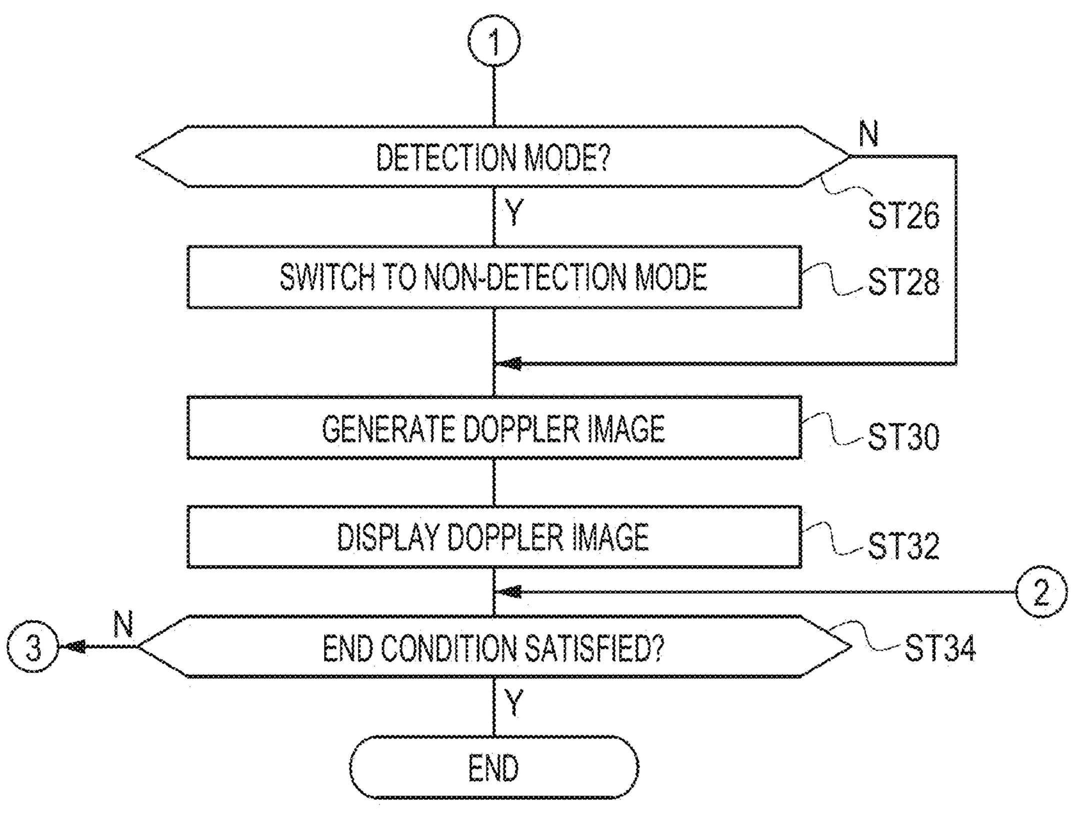
FIG. 9B is a continuation of the flowchart illustrated in FIG. 9A.

FIGS. 9A and 9B illustrate an example of the flow of the diagnostic assistance processing performed by the processor 62 of the processing apparatus 18 on the condition that diagnosis using the endoscope system 10 has started (for example, the emission of an ultrasonic wave by the ultrasound endoscope 12 has started). The flow of the diagnostic assistance processing illustrated in FIGS. 9A and 9B is an example of a "diagnostic assistance method" according to the technology of the present disclosure.

In the diagnostic assistance processing illustrated in FIG. 9A, first, in step ST10, the control unit 62C determines whether or not the currently set image mode is B-mode. In step ST10, if the currently set image mode is not B-mode (that is, in the case of Doppler mode), the determination is negative and the diagnostic assistance processing proceeds to step ST26 illustrated in FIG. 9B. In step ST10, if the currently set image mode is B-mode, the determination is positive and the diagnostic assistance processing proceeds to step ST12.

In step ST12, the control unit 62C determines whether or not the currently set operating mode is non-detection mode. In step ST12, if the currently set operating mode is not non-detection mode (that is, in the case of detection mode), the determination is negative and the diagnostic assistance processing proceeds to step ST16. In step ST12, if the currently set operating mode is non-detection mode, the determination is positive and the diagnostic assistance processing proceeds to step ST14.

In step ST14, the control unit 62C switches the operating mode from non-detection mode to detection mode. After the processing in step ST14 is executed, the diagnostic assistance processing proceeds to step ST16.

In step ST16, the generation unit 62A generates the B-mode image 24A on the basis of the reflected wave signal 74 (see FIG. 5) inputted from the transmission/reception circuit 58. After the processing in step ST16 is executed, the diagnostic assistance processing proceeds to step ST18.

In step ST18, the detection unit 62B inputs the B-mode image 24A generated in step ST16 into the trained model 78. After the processing in step ST18 is executed, the diagnostic assistance processing proceeds to step ST20.

In step ST20, the detection unit 62B uses the trained model 78 to determine whether or not a lesion is shown in the B-mode image 24A inputted into the trained model 78 in step ST18. If a lesion is shown in the B-mode image 24A, the trained model 78 outputs position-specifying information 27.

In step ST20, if a lesion is not shown in the B-mode image 24A, the determination is negative and the diagnostic assistance processing proceeds to step ST24. In step ST20, if a lesion is shown in the B-mode image 24A, the determination is positive and the diagnostic assistance processing proceeds to step ST22.

If the determination is positive in step ST20, the detection unit 62B generates the detection frame 27A on the basis of the position-specifying information 127 outputted from the trained model 78, and superimposes the detection frame 27A so as to surround the lesion area 25 onto the B-mode image 24A generated in step ST16. In step ST22, the control unit 62C displays the B-mode image 24A in which the lesion area 25 is surrounded by the detection frame 27A on the screen 26 of the display apparatus 14. Since the lesion area 25 in the B-mode image 24A is surrounded by the detection frame 27A, the physician 20 is able to visually understand the position where a lesion is shown in the B-mode image 24A. After the processing in step ST22 is executed, the diagnostic assistance processing proceeds to step ST26 illustrated in FIG. 9B.

In step ST24, the control unit 62C displays the radial ultrasound image 24 generated in step ST16 on the screen 26 of the display apparatus 14. In this case, the detection frame 27A is not attached to the B-mode image 24A, enabling the physician 20 to visually perceive that a lesion is not shown in the B-mode image 24A. After the processing in step ST24 is executed, the diagnostic assistance processing proceeds to step ST26 illustrated in FIG. 9B.

In step ST26 illustrated in FIG. 9B, the control unit 62C determines whether or not the currently set operating mode is detection mode. In step ST26, if the currently set operating mode is not detection mode (that is, in the case of non-detection mode), the determination is negative and the diagnostic assistance processing proceeds to step ST30. In step ST26, if the currently set operating mode is detection mode, the determination is positive and the diagnostic assistance processing proceeds to step ST28.

In step ST28, the control unit 62C switches the operating mode from non-detection mode to detection mode. After the processing in step ST28 is executed, the diagnostic assistance processing proceeds to step ST30.

In step ST30, the generation unit 62A generates the Doppler image 24B on the basis of the reflected wave signal 74 (see FIG. 5) inputted from the transmission/reception circuit 58. After the processing in step ST30 is executed, the diagnostic assistance processing proceeds to step ST32.

In step ST32, the control unit 62C displays the Doppler image 24B generated in step ST30 on the screen 26 of the display apparatus 14. This enables the physician 20 to visually perceive hemodynamics from the color information 24B1 (see FIG. 8) included in the Doppler image 24B displayed on the screen 26. Also, since the detection frame 27A is not included in the Doppler image 24B, the detection frame 27A does interfere with observation of the color information 24B1. After the processing in step ST32 is executed, the diagnostic assistance processing proceeds to step ST34.

In step ST34, the control unit 62C determines whether or not a condition for ending the diagnostic assistance processing (hereinafter referred to as the "diagnostic assistance end condition") is satisfied. The diagnostic assistance end condition may be a condition stipulating that the accepting apparatus 52 has accepted an instruction to end the diagnostic assistance processing, for example. In step ST34, if the diagnostic assistance end condition is not satisfied, the determination is negative and the diagnostic assistance processing proceeds to step ST10 illustrated in FIG. 9A. In step ST34, if the diagnostic assistance end condition is satisfied, the determination is positive and the diagnostic assistance processing ends.

As described above, the endoscope system 10 is selectively switched between detection mode and non-detection mode. Detection mode is an operating mode that performs detection of the lesion area 25 from the B-mode image 24A by an AI approach using the trained model 78. Non-detection mode is an operating mode that does not perform detection of the lesion area 25 from the ultrasound image 24. The trained model 78 is created using the B-mode image group 82 as supervisory data. For this reason, if processing is performed to detect the lesion area 25 from the Doppler image 24B according to the trained model 78, there is an increased likelihood of false positives in which an area other than the lesion area 25 is incorrectly detected as the lesion area 25, as compared to when processing is performed to detect the lesion area 25 from the B-mode image 24A according to the trained model 78. Also, if it is assumed that processing is performed to detect the lesion area 25 from the Doppler image 24B according to the trained model 78 and the detection frame 27A is displayed as a detection result in the Doppler image 24B, for the physician 20, the presence of the detection frame 27A may interfere with observation of the color information 24B1. Accordingly, the endoscope system 10 is switched between detection mode and non-detection mode depending on whether or not the B-mode image 24A is generated. In other words, the operating mode is switched between detection mode and non-detection mode depending on whether B-mode is set or Doppler mode is set as the image mode. This makes it possible to suppress false positives in which an area other than the lesion area 25 is incorrectly detected as the lesion area 25, and to avoid situations in which the visualization of a detection result regarding the lesion area 25 (that is, the presence of the detection frame 27A) interferes with diagnosis.

Also, in the endoscope system 10, detection mode is an operating mode used when the color information 24B1 is not superimposed onto the B-mode image 24A, while non-detection mode is an operating mode used when the color information 24B1 is superimposed onto the B-mode image 24A. In other words, detection mode is an operating mode used when the image mode is not Doppler mode (that is, in the case of B-mode), while non-detection mode is an operating mode used when the image mode is Doppler mode. Consequently, selectively using detection mode and non-detection mode in the above manner makes it possible to suppress false positives in which an area other than the lesion area 25 is incorrectly detected as the lesion area 25 due to the presence of the color information 24B1. Also, in non-detection mode, the color information 24B1 and the detection frame 27A are not displayed on the screen 26 in a mixed state, thereby making it possible to avoid situations in which the visualization of a detection result regarding the lesion area 25 (that is, the presence of the detection frame 27A) interferes with observation of the color information 24B1 included in the Doppler image 24B.

First Modification

The embodiment above gives an example in which the operating mode is switched between detection mode and non-detection mode depending on whether B-mode is set or Doppler mode is set as the image mode, but the technology of the present disclosure is not limited thereto. For example, the operating mode may also be switched between detection mode and non-detection mode depending on whether or not color information 24B1 is superimposed onto an image generated by the generation unit 62A.

Figure 10:
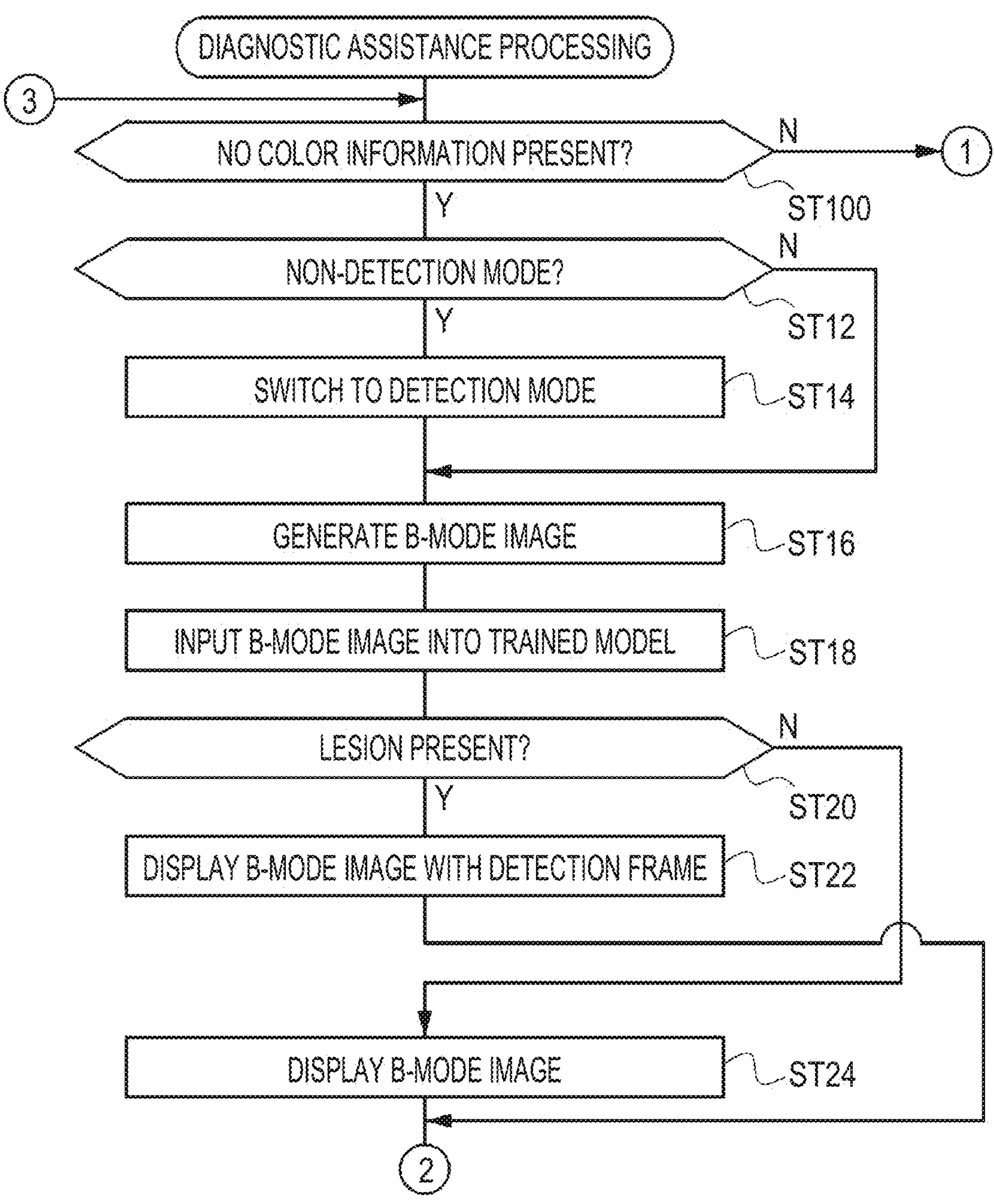
FIG. 10 is a flowchart illustrating an example of the flow of diagnostic assistance processing according to a first modification.

In this case, the diagnostic assistance processing illustrated in FIG. 10 is performed by the processor 62, for example. The flowchart illustrated in FIG. 10 differs from the flowchart illustrated in FIG. 9A in that the processing in step ST100 is applied instead of the processing in step ST10.

In step ST100 illustrated in FIG. 10, the control unit 62C performs image analysis processing on the image generated by the generation unit 62A to determine whether or not the color information 24B1 is superimposed onto an image generated by the generation unit 62A. In step ST100, if the color information 24B1 is not superimposed onto the image generated by the generation unit 62A, the determination is positive and the diagnostic assistance processing proceeds to step ST12. In step ST100, if the color information 24B1 is superimposed onto the image generated by the generation unit 62A, the determination is negative and the diagnostic assistance processing proceeds to step ST26 illustrated in FIG. 9B. This causes detection mode to be set as the operating mode when the color information 24B1 is not superimposed onto the image generated by the generation unit 62A, and causes non-detection mode to be set as the operating mode when the color information 24B1 is superimposed onto the image generated by the generation unit 62A. Consequently, similar effects as in the embodiment above are obtained.

Second Modification

The embodiment above gives an example in which, in the case of the B-mode image 24A, detection mode is set as the operating mode and detection of the lesion area 25 by an AI approach is performed on the B-mode image 24A, but depending on conditions, non-detection mode may also be set as the operating mode even in the case of the B-mode image 24A.

Figure 11:
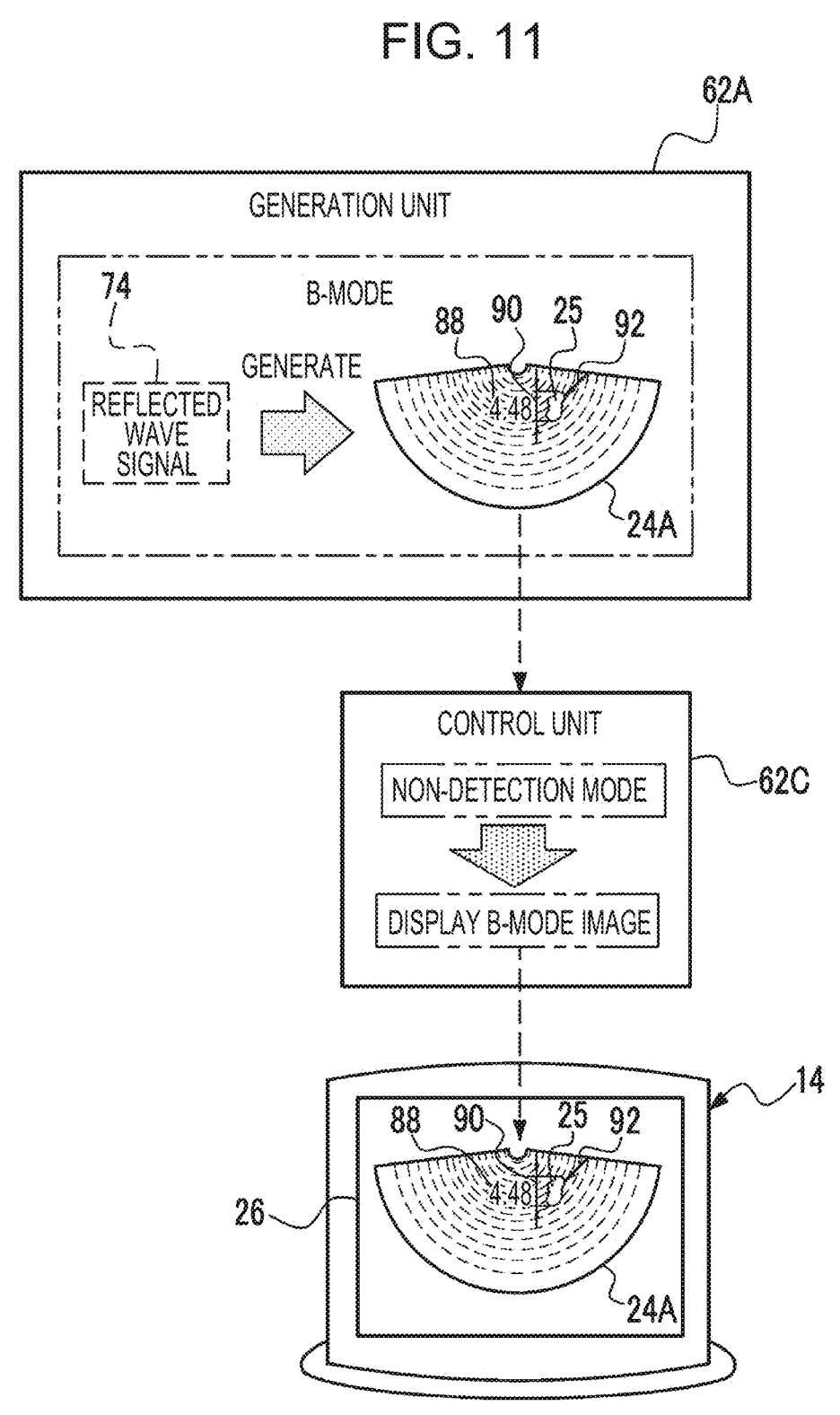

As illustrated by way of example in FIG. 11, when the generation unit 62A generates the B-mode image 24A including text information 88, a measurement line 90, and treatment assistance information 92, the control unit 62C sets non-detection mode as the operating mode. The text information 88, measurement line 90, and treatment assistance information 92 are an example of "reference information" according to the technology of the present disclosure. The text information 88 is an example of "text information" according to the technology of the present disclosure. The measurement line 90 is an example of a "measurement line" according to the technology of the present disclosure. The treatment assistance information 92 is an example of "treatment assistance information" according to the technology of the present disclosure.

The text information 88 refers to a text image (that is, an image representing text) to assist with observation of the target area of observation 72 (see FIG. 3), for example. Assisting with observation of the target area of observation 72 means, for example, serving as a reference for the physician 20 when the physician 20 identifies the presence or absence of a lesion and the position of a lesion from the B-mode image 24A. Moreover, the concept of "text" according to the present embodiment also includes numerals, symbols, and the like. Text according to the present embodiment may be text defined in Unicode, for example. In the example illustrated in FIG. 11, information visualizing the dimensions of the lesion area 25 is illustrated as an example of the text information 88

The measurement line 90 is a line used for measurement inside the target area of observation 72 (see FIG. 3), for example. In the example illustrated in FIG. 11, a dimension line that can be used to visually identify the length of the lesion area 25 in one direction is illustrated as an example of the measurement line 90. Note that although a dimension line is illustrated by way of example, this is merely one example, and the measurement line 90 may also be visualization information other than dimensionality (for example, a line used to measure a specified portion other than the lesion area 25).

The treatment assistance information 92 is information to assist with treatment using fine-needle aspiration. In the example illustrated in FIG. 11, an arrow is illustrated to point in the direction in which to insert a puncture needle when using the puncture needle as the treatment tool 42 (see FIG. 2). Note that although an arrow is illustrated by way of example, this is merely one example, and the treatment assistance information 92 may also be visualization information other than an arrow (for example, a dashed line or dotted line).

The control unit 62C performs image analysis processing on the image generated by the generation unit 62A to determine whether or not the text information 88, the measurement line 90, and/or the treatment assistance information 92 are superimposed onto an image generated by the generation unit 62A. In the example illustrated in FIG. 11, the control unit 62C determines whether or not the text information 88, the measurement line 90, and/or the treatment assistance information 92 are superimposed onto the B-mode image 24A generated by the generation unit 62A.

If the text information 88, the measurement line 90, and/or the treatment assistance information 92 are not superimposed onto the B-mode image 24A generated by the generation unit 62A, the control unit 62C sets detection mode as the operating mode. If the text information 88, the measurement line 90, and/or the treatment assistance information 92 are superimposed onto the B-mode image 24A generated by the generation unit 62A, the control unit 62C sets non-detection mode as the operating mode. In the example illustrated in FIG. 11, the text information 88, the measurement line 90, and the treatment assistance information 92 are superimposed onto the B-mode image 24A generated by the generation unit 62A, and thus non-detection mode is set as the operating mode. In this case, the control unit 62C displays the B-mode image 24A with the text information 88, the measurement line 90, and the treatment assistance information 92 superimposed thereon on the screen 26 of the display apparatus 14.

Figure 12:
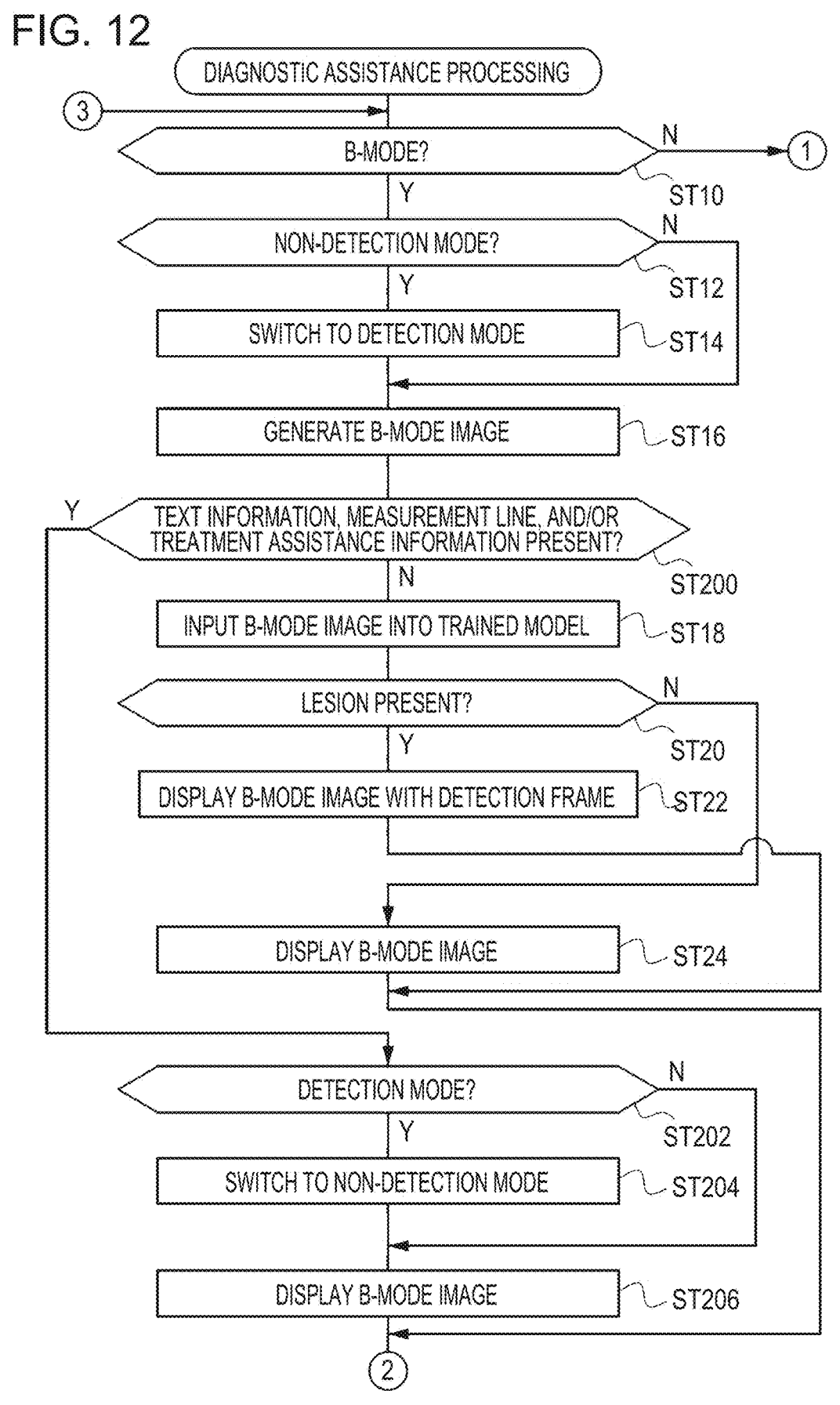

FIG. 12 illustrates an example of the flow of diagnostic assistance processing according to the second modification. The flowchart illustrated in FIG. 12 differs from the flowchart illustrated in FIG. 9A by including the processing in step ST200 between the processing in step ST16 and the processing in step ST18, and by including the processing in steps ST202 to ST206 as the processing subsequent to step ST24.

In the diagnostic assistance processing illustrated in FIG. 12, in step ST200, the control unit 62C determines whether or not the text information 88, the measurement line 90, and/or the treatment assistance information 92 are superimposed onto the B-mode image 24A generated in step ST16. In step ST200, if the text information 88, the measurement line 90, and/or the treatment assistance information 92 are not superimposed onto the B-mode image 24A generated in step ST16, the determination is negative and the diagnostic assistance processing proceeds to step ST18. In step ST200, if the text information 88, the measurement line 90, and/or the treatment assistance information 92 are superimposed onto the B-mode image 24A generated in step ST16, the determination is positive and the diagnostic assistance processing proceeds to step ST202.

In step ST202, the control unit 62C determines whether or not the currently set operating mode is detection mode. In step ST202, if the currently set operating mode is not detection mode, the determination is negative and the diagnostic assistance processing proceeds to step ST206. In step ST202, if the currently set operating mode is detection mode, the determination is positive and the diagnostic assistance processing proceeds to step ST204.

In step ST204, the control unit 62C switches the operating mode from detection mode to non-detection mode. After the processing in step ST204 is executed, the diagnostic assistance processing proceeds to step ST206.

In step ST206, the control unit 62C displays the B-mode image 24A generated in step ST16 (that is, the B-mode image 24A without attached position-specifying information 27) on the screen 26 of the display apparatus 14. In this case, the detection frame 27A is not attached to the B-mode image 24A, enabling the physician 20 to visually perceive that a lesion is not shown in the B-mode image 24A. After the processing in step ST206 is executed, the diagnostic assistance processing proceeds to step ST26 illustrated in FIG. 9B.

As illustrated in FIG. 4, the trained model 78 is created using the B-mode image group 82 as supervisory data, the B-mode image group 82 being formed from multiple B-mode images 82A without any of the text information 88, the measurement line 90, and the treatment assistance information 92 superimposed thereon. For this reason, if processing is performed to detect the lesion area 25 according to the trained model 78 from the B-mode image 24A with the text information 88, the measurement line 90, and/or the treatment assistance information 92 superimposed thereon, there is an increased likelihood of false positives in which an area other than the lesion area 25 is incorrectly detected as the lesion area 25. That is, there is an increased likelihood of false positives in which an area other than the lesion area 25 is incorrectly detected as the lesion area 25, as compared to when processing is performed to detect the lesion area 25 according to the trained model 78 from the B-mode image 24A without any of the text information 88, the measurement line 90, and/or the treatment assistance information 92 superimposed thereon. Also, if it is assumed that processing is performed to detect the lesion area 25 according to the trained model 78 from the B-mode image 24A with the text information 88, the measurement line 90, and/or the treatment assistance information 92 superimposed thereon and the detection frame 27A is displayed as a detection result in the B-mode image 24A, for the physician 20, the presence of the detection frame 27A may interfere with observation of the text information 88, the measurement line 90, and/or the treatment assistance information 92. Interfering with observation of the text information 88, the measurement line 90, and/or the treatment assistance information 92 means interfering with diagnosis by the physician 20.

Accordingly, in the second modification, the operating mode is switched between detection mode and non-detection mode depending on whether the text information 88, the measurement line 90, and/or the treatment assistance information 92 are superimposed onto the B-mode image 24A. That is, non-detection mode is set as the operating mode when the text information 88, the measurement line 90, and/or the treatment assistance information 92 are superimposed onto the B-mode image 24A, and detection mode is set as the operating mode when not any of the text information 88, the measurement line 90, and/or the treatment assistance information 92 are superimposed onto the B-mode image 24A. This makes it possible to suppress false positives in which an area other than the lesion area 25 is incorrectly detected as the lesion area 25, and to avoid situations in which the visualization of a detection result regarding the lesion area 25 (that is, the presence of the detection frame 27A) interferes with diagnosis.

Third Modification

The first modification above (that is, the example illustrated in FIG. 10) gives an example in which the operating mode is switched between detection mode and non-detection mode depending on the presence or absence of the color information 24B1, but the technology of the present disclosure is not limited thereto. For example, the operating mode may also be switched between detection mode and non-detection mode depending on the number of specific chromatic pixels superimposed onto the ultrasound image 24 generated by the generation unit 62A (for example, the number of chromatic pixels included in the color information 24B1).

Figure 13:
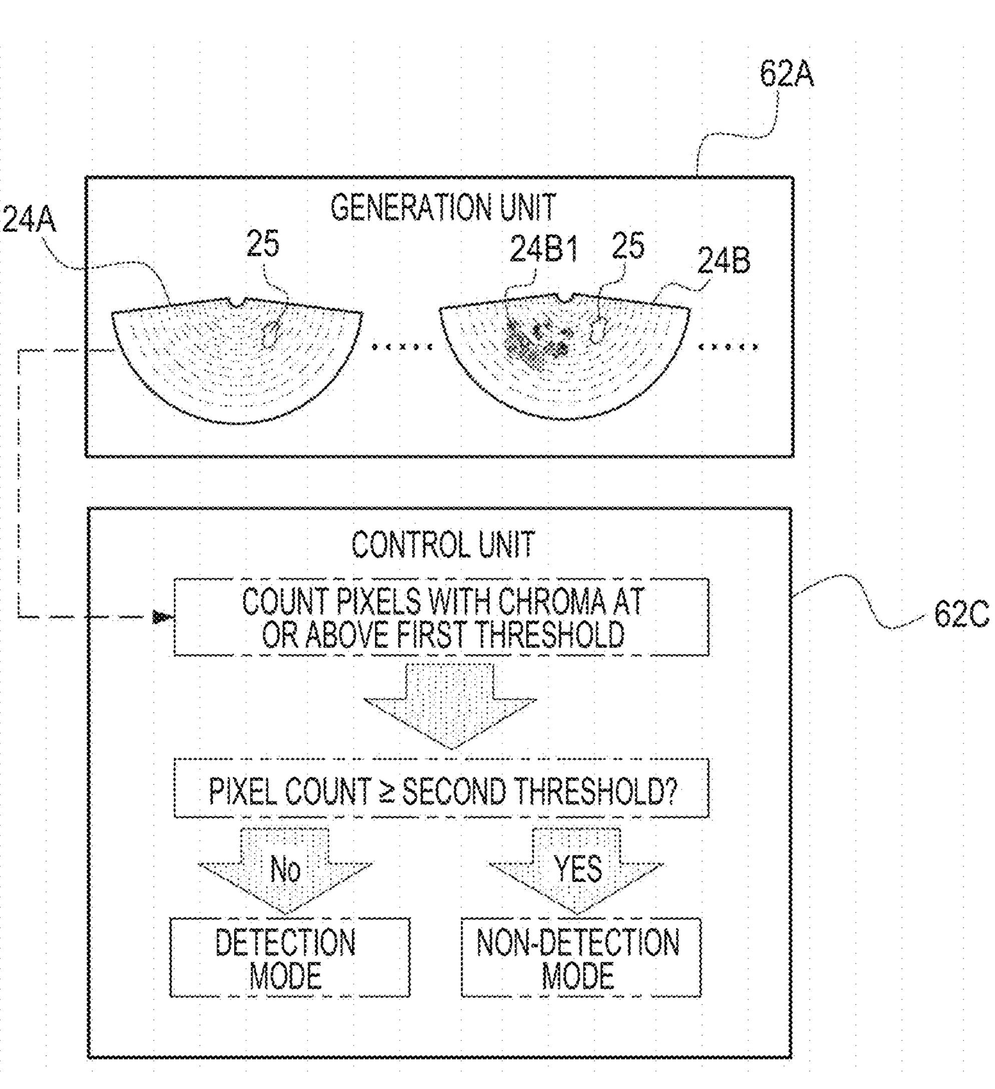
FIG. 13 is a conceptual diagram illustrating an example of details of processing by a generation unit and a control unit according to a third modification.

In this case, as illustrated by way of example in FIG. 13, the control unit 62C counts the number of pixels which are chromatic pixels having a chroma at or above a first threshold (hereinafter referred to as the "number of chromatic pixels") from the ultrasound image 24 generated by the generation unit 62A. The control unit 62C then determines whether or not the number of chromatic pixels is equal to or greater than a second threshold. The control unit 62C sets detection mode as the operating mode if the number of chromatic pixels is less than the second threshold, and sets non-detection mode as the operating mode if the number of chromatic pixels is equal to or greater than the second threshold.

The first threshold is a value set in advance as the minimum value of chroma that would trigger false positives under detection mode when chromatic pixels are included in the ultrasound image 24. The second threshold is a value set in advance as the minimum value of the number of chromatic pixels that would trigger false positives under detection mode when chromatic pixels are included in the ultrasound image 24. Note that the first threshold and/or the second threshold may also be variable values that are changed according to an instruction accepted by the accepting apparatus 52, various parameters set for the ultrasound endoscope 12, and/or the like.

As described above, in the third modification, detection mode is set when the number of chromatic pixels is less than the second threshold, and non-detection mode is set when the number of chromatic pixels is equal to or greater than the second threshold. Consequently, it is possible to suppress false positives in which an area other than the lesion area 25 is incorrectly detected as the lesion area 25 due to the presence of chromatic pixels, and to avoid situations in which the presence of chromatic pixels interferes with diagnosis by affecting the visibility of the ultrasound image 24.

Fourth Modification

The embodiment above gives an example in which non-detection mode is set as the operating mode in the case of Doppler mode, but the technology of the present disclosure is not limited thereto. For example, non-detection mode may also be set as the operating mode in the case of a first image mode or a second image mode. In the first image mode, the ultrasound image 24 is generated by using a high-frequency component included in a reflected wave obtained when an ultrasonic wave is emitted toward the target area of observation 72 and then reflected by the target area of observation 72 (hereinafter simply referred to as the "reflected wave"). In the second image mode, the B-mode image 24A is combined with a separate image.

The first image mode may be THI mode, CH mode, or CHI mode, for example. The second image mode may be Doppler mode or elastography mode, for example. Since these image modes are well known, a description is omitted here.

Figure 14:
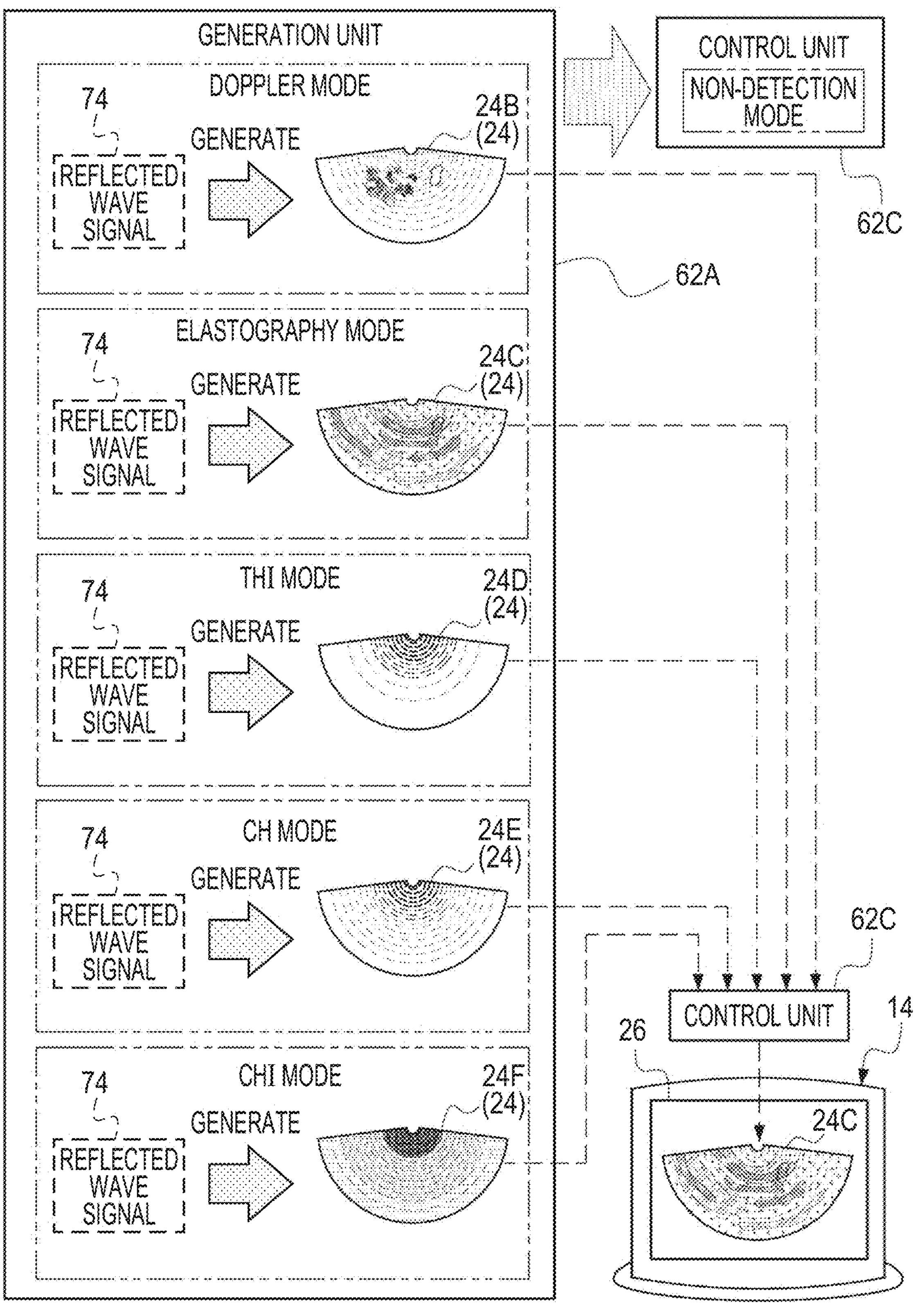
FIG. 14 is a conceptual diagram illustrating an example of details of processing by a generation unit and a control unit according to a fourth modification.

As illustrated by way of example in FIG. 14, the generation unit 62A, following an image mode instruction accepted by the accepting apparatus 52, selectively sets B-mode, Doppler mode, elastography mode, THI mode, CH mode, and CHI mode. The generation unit 62A then generates the ultrasound image 24 in accordance with the set image mode. For example, the generation unit 62A generates the Doppler image 24B in Doppler mode, generates an elastography image 24C in elastography mode, generates a THI image 24D in THI mode, generates a CH image 24E in CH mode, and generates a CHI image 24F in CHI mode.

The control unit 62C displays the ultrasound image 24 generated according to the set image mode on the screen 26 of the display apparatus 14. That is, in Doppler mode, the Doppler image 24B is displayed on the screen 26, in elastography mode, the elastography image 24C is displayed on the screen 26, in THI mode, the THI image 24D is displayed on the screen 26, in CH mode, the CH image 24E is displayed on the screen 26, and in CHI mode, the CHI image 24F is displayed on the screen 26. Note that since the elastography image 24C, the THI image 24D, the CH image 24E, and the CHI image 24F are well-known ultrasound images, a description is omitted here.

The control unit 62C sets non-detection mode as the operating mode when the first image mode or the second image mode is set (that is, when Doppler mode, elastography mode, THI mode, CH mode, or CHI mode is set).

In this way, when the first image mode is set (as an example herein, when THI mode, CH mode, or CHI mode is set), non-detection mode is set as the operating mode, thus making it possible to suppress false positives in which an area other than the lesion area 25 is incorrectly detected as the lesion area 25 due to the presence of an image area corresponding to the high-frequency component included in the reflected wave. Also, when observing the ultrasound image 24 (as an example herein, the THI image 24D, the CH image 24E, or the CHI image 24F), it is possible to avoid situations in which the presence of an image area corresponding to the high-frequency component included in the reflected wave interferes with diagnosis by affecting the visibility of the ultrasound image 24.

Also, when the second image mode is set (as an example herein, when Doppler mode or elastography mode is set), non-detection mode is set as the operating mode, thus making it possible to suppress false positives in which an area other than the lesion area 25 is incorrectly detected as the lesion area 25 due to the presence of a separate image (a chromatic image, for example) combined with a B-mode image. Also, when observing the ultrasound image 24 (as an example herein, the Doppler image 24B or the elastography image 24C), it is possible to avoid situations in which the presence of a separate image (a chromatic image, for example) combined with a B-mode image interferes with diagnosis by affecting the visibility of the ultrasound image 24.

Fifth Modification

The embodiment above describes an example in which the operating mode is switched between detection mode and non-detection mode depending on the image mode, but the technology of the present disclosure is not limited thereto, and the operating mode may also be switched between detection mode and non-detection mode according to a set value that stipulates the image quality of the ultrasound image 24.

Figure 15:
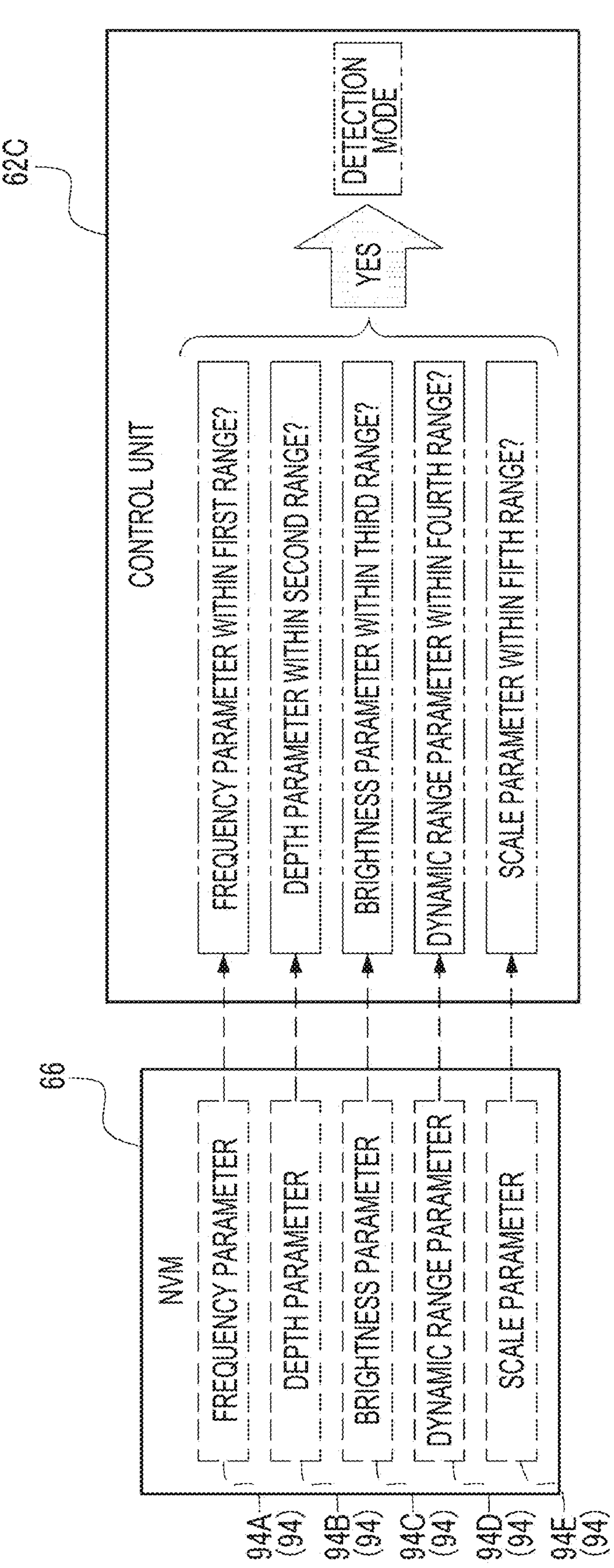
FIG. 15 is a conceptual diagram illustrating an example of details of processing by a control unit according to a fifth modification.

In this case, as illustrated in FIG. 15, for example, multiple parameters 94 are stored in the NVM 66 as set values that stipulate the image quality of the ultrasound image 24, and the control unit 62C acquires the multiple parameters 94 from the NVM 66 and switches between detection mode and non-detection mode according to the acquired multiple parameters 94. A frequency parameter 94A, a depth parameter 94B, a brightness parameter 94C, a dynamic range parameter 94D, and a magnification parameter 94E are stored as the multiple parameters 94 in the NVM 66.

The multiple parameters 94 are an example of a "set value" according to the technology of the present disclosure. The frequency parameter 94A is an example of a "frequency parameter" according to the technology of the present disclosure. The depth parameter 94B is an example of a "depth parameter" according to the technology of the present disclosure. The brightness parameter 94C is an example of a "brightness parameter" according to the technology of the present disclosure. The dynamic range parameter 94D is an example of a "dynamic range parameter" according to the technology of the present disclosure. The magnification parameter 94E is an example of a "magnification parameter" according to the technology of the present disclosure.

The frequency parameter 94A is a parameter for adjusting the frequency of the ultrasonic wave emitted from the ultrasound probe 38 (see FIG. 2). The depth parameter 94B is a parameter for adjusting the depth represented in the ultrasound image 24. The brightness parameter 94C is a parameter (namely, the gain) for adjusting the brightness of the ultrasound image 24. The dynamic range parameter 94D is a parameter for adjusting the dynamic range of the ultrasound image 24. The magnification parameter 94E is a parameter for adjusting the scale of a digital zoom for the ultrasound image 24.

The control unit 62C sets detection mode as the operating mode when the following condition (hereinafter referred to as the "parameter condition") is met: the frequency parameter 94A is within a first range, the depth parameter 94B is within a second range, the brightness parameter 94C is within a third range, the dynamic range parameter 94D is within a fourth range, and the magnification parameter 94E is within a fifth range. The control unit 62C set non-detection mode as the operating mode when the parameter condition is not met. Note that the first to fifth ranges are specified in advance. The first to fifth ranges are an example of a "specified range" according to the technology of the present disclosure.

The first range is an ideal range of the frequency of the ultrasonic wave emitted from the ultrasound probe 38. The ideal range of the frequency of the ultrasonic wave may be, for example, a range of frequencies in which an area other than the lesion area 25 is not incorrectly detected as the lesion area 25 (for example, a range of frequencies applied to all of the B-mode images 82A included in the B-mode image group 82).

The second range is an ideal range of the depth represented in the ultrasound image 24. The ideal range of the depth may be, for example, a range of depths in which an area other than the lesion area 25 is not incorrectly detected as the lesion area 25 (for example, a range of depths applied to all of the B-mode images 82A included in the B-mode image group 82).

The third range is an ideal range of the brightness of the ultrasound image 24. The ideal range of the brightness may be, for example, a range of brightnesses in which an area other than the lesion area 25 is not incorrectly detected as the lesion area 25 (for example, a range of brightnesses applied to all of the B-mode images 82A included in the B-mode image group 82).

The fourth range is an ideal range of the dynamic range of the ultrasound image 24. The ideal range of the dynamic range may be, for example, a range of dynamic ranges in which an area other than the lesion area 25 is not incorrectly detected as the lesion area 25 (for example, a range of dynamic ranges applied to all of the B-mode images 82A included in the B-mode image group 82).

The fifth range is an ideal range of the scale of the digital zoom for the ultrasound image 24. The ideal range of the scale of the digital zoom may be, for example, a range of scales of the digital zoom in which an area other than the lesion area 25 is not incorrectly detected as the lesion area 25 (for example, a range of scales of the digital zoom applied to all of the B-mode images 82A included in the B-mode image group 82).

According to the fifth modification, the operating mode is switched between detection mode and non-detection mode according to the multiple parameters 94. That is, detection mode is set when the parameter condition is satisfied, and non-detection mode is set when the parameter condition is not satisfied. Therefore, it is possible to suppress false positives in which an area other than the lesion area 25 is incorrectly detected as the lesion area 25 due to the multiple parameters 94 not being within ideal ranges, and to avoid situations in which the multiple parameters 94 not being within ideal ranges interferes with diagnosis by affecting the visibility of the ultrasound image 24.

Also, according to the fifth modification, detection mode is set when the frequency parameter 94A is within the first range, and non-detection mode is set when the frequency parameter 94A is not within the first range. Therefore, it is possible to suppress false positives in which an area other than the lesion area 25 is incorrectly detected as the lesion area 25 due to the frequency parameter 94A not being within the first range, and to avoid situations in which the frequency parameter 94A not being within the first range interferes with diagnosis by affecting the visibility of the ultrasound image 24.

Also, according to the fifth modification, detection mode is set when the depth parameter 94B is within the second range, and non-detection mode is set when the depth parameter 94B is not within the second range. Therefore, it is possible to suppress false positives in which an area other than the lesion area 25 is incorrectly detected as the lesion area 25 due to the depth parameter 94B not being within the second range, and to avoid situations in which the depth parameter 94B not being within the second range interferes with diagnosis by affecting the visibility of the ultrasound image 24.

Also, according to the fifth modification, detection mode is set when the brightness parameter 94C is within the third range, and non-detection mode is set when the brightness parameter 94C is not within the third range. Therefore, it is possible to suppress false positives in which an area other than the lesion area 25 is incorrectly detected as the lesion area 25 due to the brightness parameter 94C not being within the third range, and to avoid situations in which the brightness parameter 94C not being within the third range interferes with diagnosis by affecting the visibility of the ultrasound image 24.

Also, according to the fifth modification, detection mode is set when the dynamic range parameter 94D is within the fourth range, and non-detection mode is set when the dynamic range parameter 94D is not within the fourth range. Therefore, it is possible to suppress false positives in which an area other than the lesion area 25 is incorrectly detected as the lesion area 25 due to the dynamic range parameter 94D not being within the fourth range, and to avoid situations in which the dynamic range parameter 94D not being within the fourth range interferes with diagnosis by affecting the visibility of the ultrasound image 24.

Also, according to the fifth modification, detection mode is set when the magnification parameter 94E is within the fifth range, and non-detection mode is set when the magnification parameter 94E is not within the fifth range. Therefore, it is possible to suppress false positives in which an area other than the lesion area 25 is incorrectly detected as the lesion area 25 due to the magnification parameter 94E not being within the fifth range, and to avoid situations in which the magnification parameter 94E not being within the fifth range interferes with diagnosis by affecting the visibility of the ultrasound image 24.

Also, according to the fifth modification, the multiple parameters 94 are stored in the NVM 66, and the operating mode is switched between detection mode and non-detection mode by the control unit 62C according to the multiple parameters 94 in the NVM 66. Therefore, the operating mode can be set according to the multiple parameters 94 without having to manually input the multiple parameters 94 used to determine switching between detection mode and non-detection mode every time the ultrasound image 24 is generated.

Note that although the multiple parameters 94 are given by way of example herein, the technology of the present disclosure is not limited thereto, and the operating mode may also be switched between detection mode and non-detection mode depending on whether or not at least one of the multiple parameters 94 is within a range specified in advance (that is, the ideal range described above).

Sixth Modification

The fifth modification gives an example in which the multiple parameters 94 stored in the NVM 66 are acquired by the control unit 62C and the control unit 62C switches between detection mode and non-detection mode according to the multiple parameters 94, but the technology of the present disclosure is also achieved in the case where the multiple parameters 94 are not stored in the NVM 66.

Figure 16:
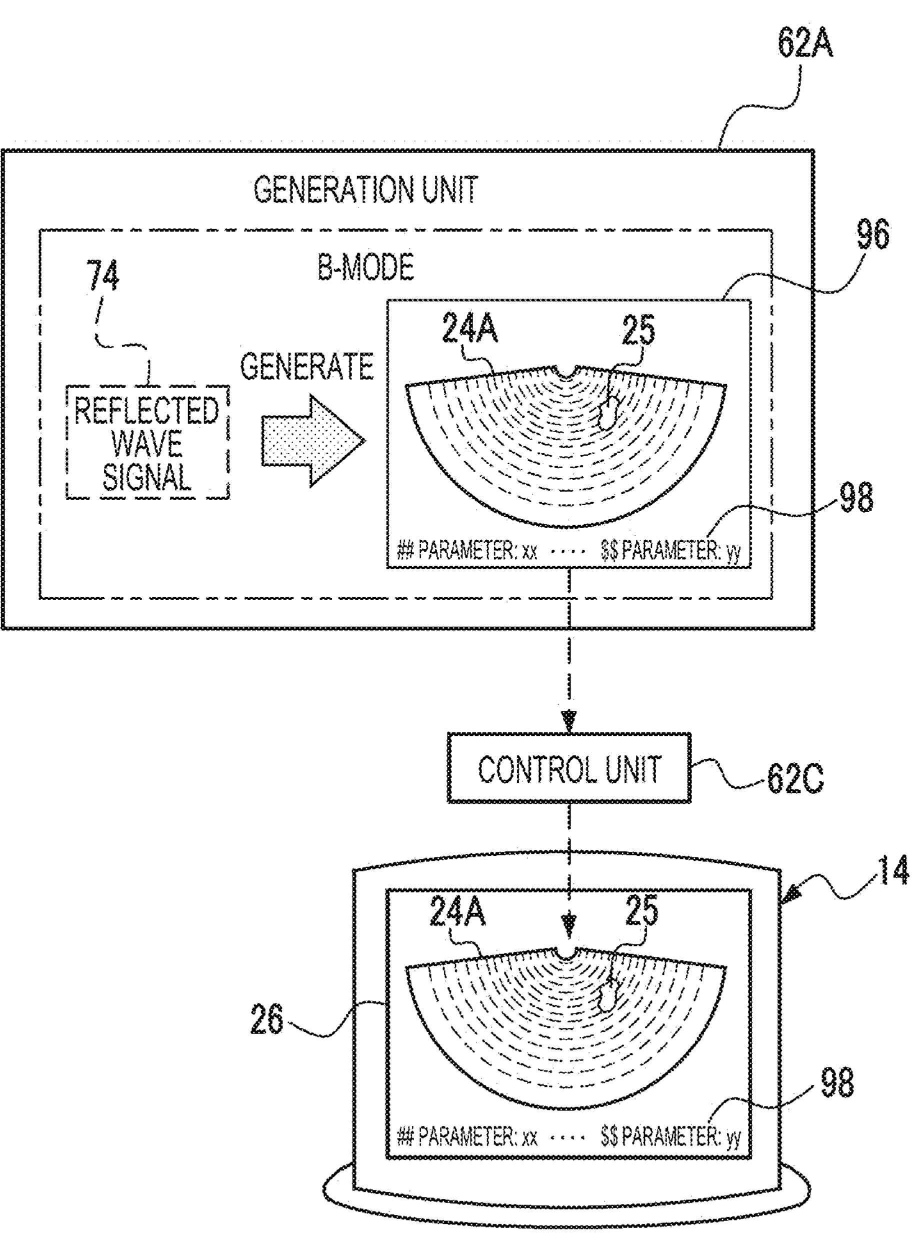
FIG. 16 is a conceptual diagram illustrating an example of details of processing by a generation unit and a control unit according to a sixth modification.

In this case, for example, as illustrated in FIG. 16, the generation unit 62A generates a frame 96 in B-mode. The frame 96 contains the B-mode image 24A, with a text image 98 superimposed. The text image 98 is an image of the multiple parameters 94 expressed as text. The control unit 62C displays the frame 96 on the screen 26 of the display apparatus 14. With this arrangement, the B-mode image 24A and the text image 98 are displayed on the screen 26, enabling the physician 20 to observe the B-mode image 24A and grasp the multiple parameters 94 indicated by the text image 98.

Figure 17:
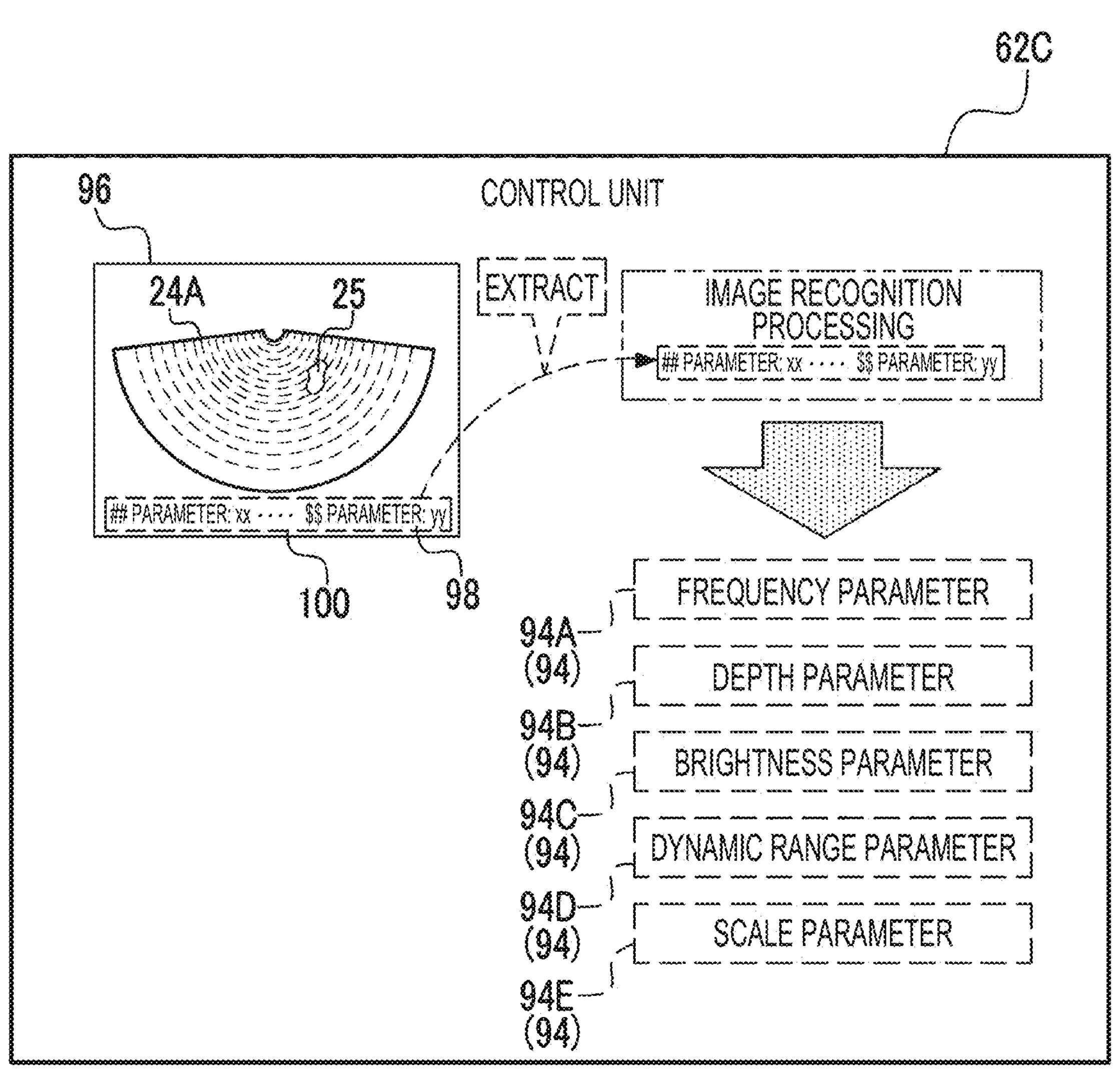
FIG. 17 is a conceptual diagram illustrating an example of details of processing by a control unit according to a sixth modification.

As illustrated by way of example in FIG. 17, the control unit 62C identifies an area 100 where the text image 98 is present from the frame 96, and extracts the identified area 100 from the frame 96. The control unit 62C then performs image recognition processing (for example, image recognition processing by an AI approach, or image recognition processing by a non-AI approach such as template matching) on the area 100 extracted from the frame 96, thereby recognizing and acquiring the multiple parameters 94 from the text image 98 included in the area 100. The control unit 62C then switches between detection mode and non-detection mode according to the multiple parameters 94, in a manner similar to the fifth modification above. With this arrangement, similar effects as in the fifth modification above are obtained.

Seventh Modification

In the embodiment above, the frequency at which the lesion area 25 is detected from the ultrasound image 24 (hereinafter referred to as the "detection frequency"), the precision with which the lesion area 25 is detected from the ultrasound image 24 (hereinafter referred to as the "detection precision"), and the target to be detected as the lesion area 25 from the ultrasound image 24 (hereinafter referred to as the "detection target") are not changed, irrespectively of the image mode, but the processor 62 may also differentiate the detection frequency, the detection precision, and/or the detection target depending on the image mode.

When differentiating the detection frequency depending on the image mode, for example, the detection frequency is differentiated between the case of using B-mode as the main image mode and the case of using an image mode other than B-mode (elastography mode, for example) as the main image mode. In this case, the detection frequency in B-mode is set higher than the detection frequency in the image mode other than B-mode (hereinafter referred to as the "other image mode"). For example, the detection frequency in B-mode is set to once every frame, and the detection frequency in the other image mode is set to once every multiple frames (once every two frames, for example).

When differentiating the detection precision depending on the image mode, for example, the detection precision is differentiated between the case of using B-mode as the main image mode and the case of using the other image mode as the main image mode. As a first example, the method for differentiating the detection precision may be a method that differentiates the amount of training performed on the model 80 to obtain the trained model 78 for use in B-mode and the amount of training performed on a model to obtain a trained model for use in the other image mode. As a second example, the method for differentiating the detection precision may be a method that differentiates the number of intermediate layers in the trained model 78 for use in B-mode and the number of intermediate layers in a trained model for use in the other image mode.

When differentiating the detection target depending on the image mode, for example, the detection target is differentiated between the case of using B-mode as the main image mode and the case of using the other image mode as the main image mode. The method for differentiating the detection target may be, for example, a method that generates the trained model 78 for use in B-mode by training the model 80 to detect lesions of a first type and using the obtained trained model, and generates a trained model for use in the other image mode by training the model 80 to detect lesions of a second type (that is, lesions of a different type than the first type).

Figure 18:
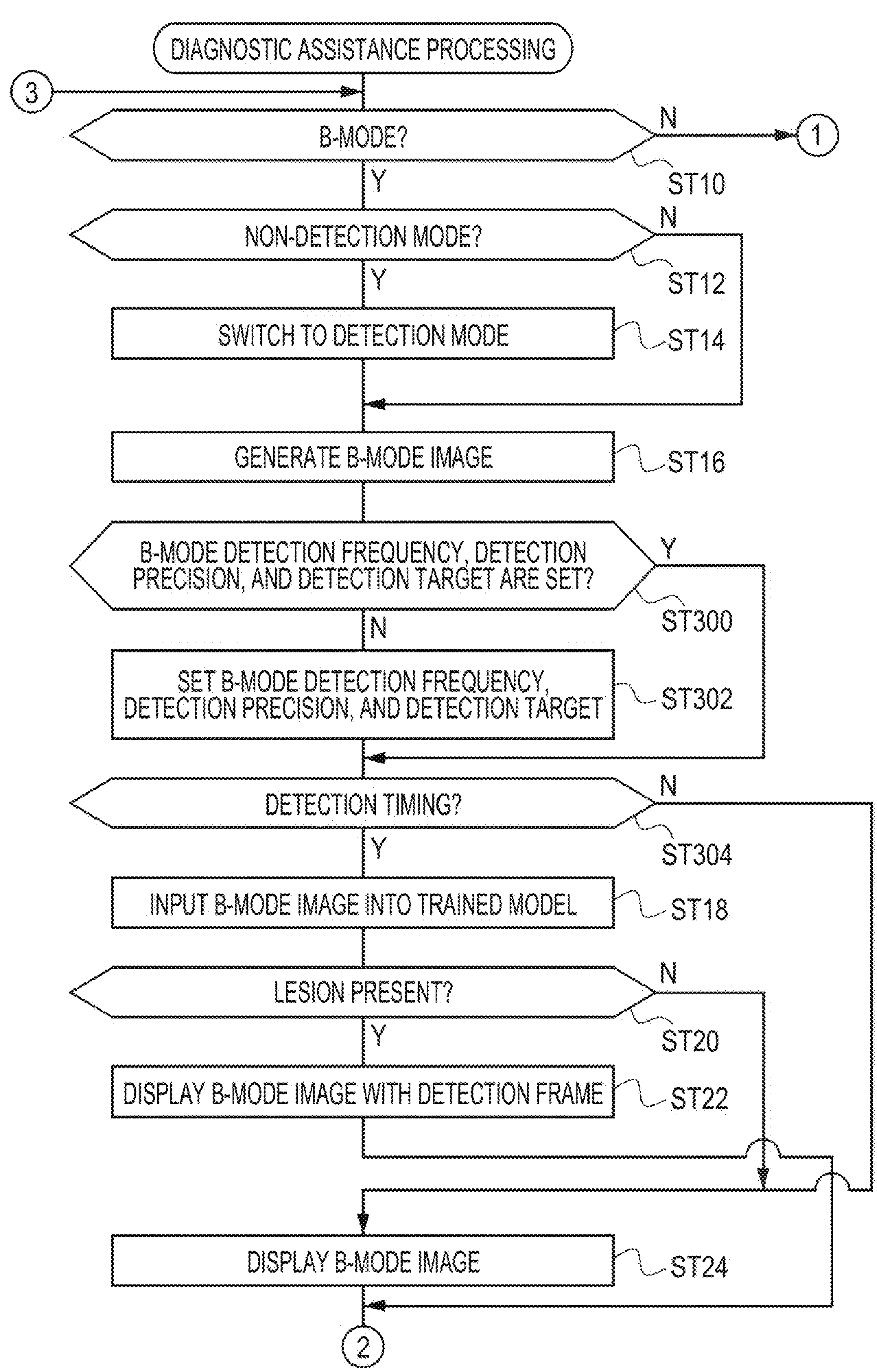
FIG. 18 is a flowchart illustrating an example of the flow of diagnostic assistance processing according to a seventh modification.

FIG. 18 illustrates an example of the flow of diagnostic assistance processing according to the seventh modification. The flowchart illustrated in FIG. 18 differs from the flowchart illustrated in FIG. 9A by including the processing in steps ST300 to ST304 between the processing in step ST16 and the processing in step ST18.

In the diagnostic assistance processing illustrated in FIG. 18, in step ST300, the control unit 62C determines whether or not the detection frequency, detection precision, and detection target are set for B-mode. In step ST300, if the detection frequency, detection precision, and detection target are set for B-mode, the determination is positive and the diagnostic assistance processing proceeds to step ST304. In step ST300, if the detection frequency, detection precision, and detection target are not set for B-mode, the determination is negative and the diagnostic assistance processing proceeds to step ST302.

In step ST302, the control unit 62C sets the detection frequency, detection precision, and detection target for B-mode. After the processing in step ST302 is executed, the diagnostic assistance processing proceeds to step ST304.

In step ST304, the control unit 62C determines whether a timing at which to detect the lesion area 25 has been reached. The timings at which to detect the lesion area 25 are, for example, timings separated by a time interval defined by the reciprocal of the frame rate. In step ST304, if a timing at which to detect the lesion area 25 has not been reached, the determination is negative and the diagnostic assistance processing proceeds to step ST24. In step ST304, if a timing at which to detect the lesion area 25 has been reached, the determination is positive and the diagnostic assistance processing proceeds to step ST18.

As described above, according to the seventh modification, the detection frequency is differentiated depending on the image mode, thus making it possible to avoid situations in which the lesion area 25 is detected too many times or too few times according to the image mode. Also, according to the seventh modification, the detection precision is differentiated depending on the image mode, thus making it possible to avoid situations in which the precision of detecting the lesion area 25 is reduced according to the image mode. Furthermore, according to the seventh modification, the detection target is differentiated depending on the image mode, thus making it possible to avoid situations in which an unintended portion is detected as the lesion area 25.

The seventh modification gives an example in which the detection frequency, detection precision, and/or detection target are differentiated depending on the image mode, but the technology of the present disclosure is not limited thereto. For example, the detection frequency, detection precision, and/or detection target may also be differentiated depending on whether or not reference information (for example, the text information 88, measurement line 90, and/or treatment assistance information 92) is superimposed onto the B-mode image 24A, or according to a set value (for example, the multiple parameters 94) that stipulates the image quality of the ultrasound image 24.

Other Modifications

The embodiment above gives an example in which detection mode is set as the operating mode in the case of B-mode, but the technology of the present disclosure is not limited thereto. For example, detection mode may also be set as the operating mode in the case of A-mode, M-mode, or the like rather than B-mode, or detection mode may simply be set as the operating mode in the case of an image mode designated in advanced as the single main image mode. The main image mode may be the image mode corresponding to the type of ultrasound images 24 used to train the model 80. For example, if the ultrasound images 24 used to train the model 80 are A-mode images, the main image mode is A-mode, and if the ultrasound images 24 used to train the model 80 are M-mode images, the main image mode is M-mode.

The embodiment above gives an example in which the lesion area 25 is detected, but the technology of the present disclosure is not limited thereto, and a specific area (for example, a specific organ) other than the lesion area 25 may also be detected together with the lesion area 25 or instead of the lesion area 25.

The embodiment above gives an example of detecting the lesion area 25 by an AI approach (that is, an example of detecting the lesion area 25 according to the trained model 78), but the technology of the present disclosure is not limited thereto, and the lesion area 25 may also be detected by a non-AI approach. The detection method by a non-AI approach may be a detection method using template matching, for example. In this case, a template used for template matching is an example of "detection assistance information" according to the technology of the present disclosure.

The embodiment above illustrates the ultrasound endoscope 12 by way of example, but the technology of the present disclosure is also achieved with an extracorporeal diagnostic ultrasound apparatus.

The embodiment above gives an example in which the ultrasound image 24 and the detection frame 27A generated by the processing apparatus 18 are displayed on the screen 26 of the display apparatus 14, but the ultrasound image 24 with an attached detection frame 27A may also be transmitted to various apparatuses such as a server, PC, and/or tablet terminal and stored in a memory of the various apparatuses. The ultrasound image 24 with an attached detection frame 27A may also be recorded in a report. The position-specifying information 27 may also be stored in a memory of various apparatuses, and may also be recorded in a report. The ultrasound image 24, detection frame 27A, and/or position-specifying information 27 are preferably stored in a memory and recorded in a report for each subject 22.

The embodiment above is described using an example in which the diagnostic assistance processing is performed by the processing apparatus 18, but the technology of the present disclosure is not limited thereto. The diagnostic assistance processing may also be performed by the processing apparatus 18 and at least one apparatus provided externally to the processing apparatus 18, or may be performed by only the at least one apparatus provided externally to the processing apparatus 18 (for example, an auxiliary processing apparatus which is connected to the processing apparatus 18 and which is used to extend the functionality of the processing apparatus 18).

One example of the at least one apparatus provided externally to the processing apparatus 18 is a server. The server may also be realized by cloud computing. Cloud computing is merely one example, and the server may also be realized by network computing such as fog computing, edge computing, or grid computing. Also, the server given as the at least one apparatus provided externally to the processing apparatus 18 is merely one example, and instead of a server, the apparatus may also be at least one PC and/or at least one mainframe or the like, and may also be at least one server, at least one PC, and/or at least one mainframe or the like.

The embodiment above gives an example in which the ultrasound image 24 with the detection frame 27A superimposed thereon is displayed on the screen 26 of the display apparatus 14, but this is merely one example. For example, the ultrasound image 24 with the detection frame 27A superimposed thereon and the ultrasound image 24 without the detection frame 27A superimposed thereon (that is, the ultrasound image 24 in which the result of detecting the lesion area 25 is not visualized) may also be displayed on separate screens.

In the embodiment above, the physician 20 is made to perceive the presence or absence of a lesion and the position of the lesion, but the physician 20 may also be made to perceive the type of lesion, the progress of lesion, and/or the like. In this case, ultrasound images (in the example illustrated in FIG. 4, the B-mode images 82A) with information that can be used to identify the type of lesion, progress of lesion, and/or the like included in the annotation 86 may simply be used as supervisory data to train the model 80.

The embodiment above is described using an example in which the diagnostic assistance program 76 is stored in the NVM 66, but the technology of the present disclosure is not limited thereto. For example, the diagnostic assistance program 76 may also be stored in an SSD or a portable storage medium such as a USB memory. The storage medium is a non-transitory computer readable storage medium. The diagnostic assistance program 76 stored in the storage medium is installed in the computer 54. The processor 62 executes the diagnostic assistance processing according to the diagnostic assistance program 76.

In the embodiment above, the computer 54 is illustrated by way of example, but the technology of the present disclosure is not limited thereto, and a device including an ASIC, an FPGA, and/or a PLD may also be applied in place of the computer 54. A combination of a hardware configuration and a software configuration may also be used in place of the computer 54.

The various types of processors indicated below can be used as hardware resources to execute the diagnostic assistance processing described in the embodiment above. The processor may be, for example, a general-purpose processor that executes software, namely a program, to thereby function as hardware resources to execute the diagnostic assistance processing. The processor may also be, for example, a special-purpose electronic circuit such as an FPGA, a PLD, or an ASIC, that is, a processor having a specially designed circuit configuration for executing specific processing. Any of these processors has a built-in or connected memory, and any of these processors uses the memory to execute the diagnostic assistance processing.

The hardware resources to execute the diagnostic assistance processing may be formed from one of these various types of processors, or may be formed from a combination of two or more processors of the same or different types (such as a combination of multiple FPGAs, or a combination of a processor and an FPGA). The hardware resources to execute the diagnostic assistance processing may also be a single processor.

As a first example of a configuration using a single processor, a combination of one or more processors and software are used to form a single processor, and this processor functions as the hardware resources to execute the diagnostic assistance processing. A second example is to use processor in which the functions of the entire system, including multiple hardware resources to execute the diagnostic assistance processing, are realized by a single IC (Integrated Circuit) chip, as typified by an SoC. In this way, the diagnostic assistance processing is realized by using one or more of the various types of processors above as hardware resources.

Furthermore, an electronic circuit combining circuit elements such as semiconductor elements can be used more specifically as the hardware structure of these various types of processors. Also, the diagnostic assistance processing above is merely one example. Needless to say, unnecessary steps may be deleted, new steps may be added, and the processing sequence may be rearranged, insofar as the result does not depart from the gist of the technology of the present disclosure.

The descriptions and illustrations given above are detailed descriptions of portions related to the technology of the present disclosure, and are nothing more than examples of the technology of the present disclosure. For example, the above descriptions pertaining to configuration, function, action, and effect are descriptions pertaining to one example of the configuration, function, action, and effect of portions related to the technology of the present disclosure. Needless to say, unnecessary portions may be deleted and new elements may be added or substituted with respect to the descriptions and illustrations given above, insofar as the result does not depart from the gist of the technology of the present disclosure. Also, to avoid confusion and to facilitate understanding of the portions related to the technology of the present disclosure, in the descriptions and illustrations given above, description is omitted in regard to common technical knowledge and the like that does not require particular explanation to enable implementation of the technology of the present disclosure.

In this specification, "A and/or B" is synonymous with "at least one of A or B". That is, "A and/or B" means that: A only is a possibility; B only is a possibility; and a combination of A and B is a possibility. Also, in this specification, the same way of thinking as for "A and/or B" also applies when three or more matters are expressively linked using "and/or".

All documents, patent applications, and technical standards mentioned in this specification are incorporated by reference herein to the same extent that individual documents, patent applications, and technical standards are specifically and individually noted as being incorporated by reference.

What is claimed is:

1. A diagnostic assistance apparatus comprising:

a processor, wherein the processor is configured to:

acquire a first ultrasound image which is generated by an ultrasound endoscope and which shows a target area of observation; and switch between a first operating mode and a second operating mode according to whether or not reference information referenced to diagnose the target area of observation is combined with the first ultrasound image, according to whether or not the first ultrasound image is an image obtained in an auxiliary image mode, which is an image mode other than a main image mode, or according to a set value that stipulates the image quality of the first ultrasound image, wherein:

the first operating mode is an operating mode that performs detection of a specific area from the first ultrasound image on the basis of detection assistance information created using a second ultrasound image obtained in the main image mode, and the second operating mode is an operating mode that performs detection of the specific area but does not output a detection result, or that does not perform detection of the specific area.

2. The diagnostic assistance apparatus according to claim 1, wherein:

the first operating mode is an operating mode used in a case in which the reference information is not combined with the first ultrasound image, and the second operating mode is an operating mode used in a case in which the reference information is combined with the first ultrasound image.

3. The diagnostic assistance apparatus according to claim 1, wherein:

the first operating mode is an operating mode used in a case in which the first ultrasound image is not an image obtained in the auxiliary image mode, and the second operating mode is an operating mode used in a case in which the first ultrasound image is an image obtained in the auxiliary image mode.

4. The diagnostic assistance apparatus according to claim 1, wherein:

the first operating mode is an operating mode used in a case in which the set value is within a specified range, and the second operating mode is an operating mode used in a case in which the set value is not within the specified range.

5. The diagnostic assistance apparatus according to claim 1, wherein:

the reference information includes color information expressing characteristics in the target area of observation as colors.

6. The diagnostic assistance apparatus according to claim 5, wherein:

the color information includes a plurality of chromatic pixels, the first operating mode is an operating mode used in a case in which the number of chromatic pixels having a chroma exceeding a first threshold from among the plurality of chromatic pixels is less than a second threshold, and the second operating mode is an operating mode used in a case in which the number is equal to or greater than the second threshold.

7. The diagnostic assistance apparatus according to claim 1, wherein:

the reference information includes text information assisting with observation of the target area of observation.

8. The diagnostic assistance apparatus according to claim 1, wherein:

the reference information includes a measurement line used for measurement in the target area of observation.

9. The diagnostic assistance apparatus according to claim 1, wherein:

the reference information includes treatment assistance information assisting with treatment using fine-needle aspiration.

10. The diagnostic assistance apparatus according to claim 1, wherein:

the auxiliary image mode is a first image mode that generates an ultrasound image using a high-frequency component included in a reflected wave obtained in a case in which an ultrasonic wave is emitted toward the target area of observation and then reflected by the target area of observation, or a second image mode that combines a B-mode image with a separate image.

11. The diagnostic assistance apparatus according to claim 10, wherein:

the first image mode is THI (tissue harmonic imaging) mode, CH (compound harmonic) mode, or CHI (contrast harmonic imaging) mode, and the second image mode is Doppler mode or elastography mode.

12. The diagnostic assistance apparatus according to claim 1, wherein:

the set value includes a frequency parameter for adjusting the frequency of an ultrasonic wave emitted from the ultrasound endoscope, a depth parameter for adjusting depth represented in the first ultrasound image, a brightness parameter for adjusting the brightness of the first ultrasound image, a dynamic range parameter for adjusting the dynamic range of the first ultrasound image, and/or a magnification parameter for adjusting the scale of a digital zoom for the first ultrasound image.

13. The diagnostic assistance apparatus according to claim 1, wherein:

the ultrasound endoscope has the set value, and the processor is configured to acquire the set value from the ultrasound endoscope.

14. The diagnostic assistance apparatus according to claim 1, wherein:

a text image that can be used to identify the set value is combined with a frame containing the first ultrasound image, and the processor is configured to:

identify the set value by performing image recognition processing on the text image; and switch between the first operating mode and the second operating mode according to the identified set value.

15. The diagnostic assistance apparatus according to claim 1, wherein:

the processor is configured to detect the specific area from the first ultrasound image by an AI (artificial intelligence) approach.

16. The diagnostic assistance apparatus according to claim 1, wherein:

the detection assistance information is a trained model obtained by training a model on supervisory data that includes the second ultrasound image.

17. The diagnostic assistance apparatus according to claim 1, wherein:

the processor is configured to differentiate a frequency at which to detect the specific area from the first ultrasound image, a precision with which to detect the specific area from the first ultrasound image, and/or a target to be detected as the specific area from the first ultrasound image according to the reference information, the auxiliary image mode, and/or the set value.

18. An ultrasound endoscope comprising:

the diagnostic assistance apparatus according to claim 1; and an ultrasound endoscope main body to which the ultrasound endoscope is connected.

19. A diagnostic assistance method comprising:

acquiring a first ultrasound image which is generated by an ultrasound endoscope and which shows a target area of observation; and switching between a first operating mode and a second operating mode according to whether or not reference information referenced to diagnose the target area of observation is combined with the first ultrasound image, according to whether or not the first ultrasound image is an image obtained in an auxiliary image mode, which is an image mode other than a main image mode, or according to a set value that stipulates the image quality of the first ultrasound image, wherein:

the first operating mode is an operating mode that performs detection of a specific area from the first ultrasound image on the basis of detection assistance information created using a second ultrasound image obtained in the main image mode, and the second operating mode is an operating mode that performs detection of the specific area but does not output a detection result, or that does not perform detection of the specific area.

20. A non-transitory computer-readable storage medium storing a program executable by a computer to execute a process comprising:

acquiring a first ultrasound image which is generated by an ultrasound endoscope and which shows a target area of observation; and switching between a first operating mode and a second operating mode according to whether or not reference information referenced to diagnose the target area of observation is combined with the first ultrasound image, according to whether or not the first ultrasound image is an image obtained in an auxiliary image mode, which is an image mode other than a main image mode, or according to a set value that stipulates the image quality of the first ultrasound image, wherein:

the first operating mode is an operating mode that performs detection of a specific area from the first ultrasound image on the basis of detection assistance information created using a second ultrasound image obtained in the main image mode, and the second operating mode is an operating mode that performs detection of the specific area but does not output a detection result, or that does not perform detection of the specific area.

* * * * *